(12) United States Patent
Benson et al.

(10) Patent No.: US 8,008,503 B2
(45) Date of Patent: Aug. 30, 2011

(54) METHYL-BENZIMIDAZOLE DERIVATIVES

(75) Inventors: Gregory Martin Benson, Therwil (CH); Konrad Bleicher, Freiburg (DE); Uwe Grether, Efringen-Kirchen (DE); Rainer E Martin, Basel (CH); Jean-Marc Plancher, Hagenthal-le-Bas (FR); Hans Richter, Grenzach-Wyhlen (DE); Sven Taylor, Riedisheim (FR); Minmin Yang, Shanghai (CN)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/862,823

(22) Filed: Aug. 25, 2010

(65) Prior Publication Data

US 2010/0331371 A1 Dec. 30, 2010

Related U.S. Application Data

(62) Division of application No. 12/265,049, filed on Nov. 5, 2008, now Pat. No. 7,825,258.

(30) Foreign Application Priority Data

Nov. 15, 2007 (EP) .................................. 07120737

(51) Int. Cl.
*A61K 31/4184* (2006.01)
*C07D 235/06* (2006.01)
(52) U.S. Cl. .................................. 548/309.7; 514/394
(58) Field of Classification Search ............. 548/309.7
See application file for complete search history.

(56) References Cited

U.S. PATENT DOCUMENTS

2006/0148805 A1 7/2006 Chen et al.

FOREIGN PATENT DOCUMENTS

WO 03/066629 A 8/2003

OTHER PUBLICATIONS

Gross, et al., The Peptides, vol. 2, pp. 365-381 (1980) Academic Press, NY.
Tempest et al., Tet. Lett., 42, pp. 4959-4962 (2001).
Tempest et al., Tet. Lett., 42, pp. 4963-4968 (2001).
Zhang et al., Tet Lett., 45, pp. 6757-6760 (2004).
Bamford et al., Bioorganic & Medicinal Chemistry Letters, 15, pp. 3402-3406 (2005).
Reeve et al., J. Am. Chem. Soc., 82, pp. 4062-4066 (1960).
Carlsson et al., Helv. Chim. Acta, 46, pp. 2271-2285 (1963).
White, E.H., J. Am. Chem. Soc., 77, pp. 6011-6014 (1955).
Evans et al., Tetrahedron Lett., 38, pp. 4535-4538 (1997).
Seto et al., J. Am. Chem. Soc., 115, pp. 1321-1329 (1993).

*Primary Examiner* — Laura L. Stockton
(74) *Attorney, Agent, or Firm* — George W. Johnston; Dennis P. Tramaloni; Brian C. Remy

(57) ABSTRACT

The invention is concerned with novel substituted benzimidazole derivatives of formula (I)

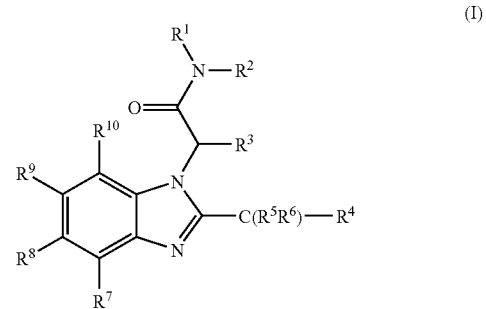

wherein $R^1$ to $R^{10}$ are as defined in the description and in the claims, as well as physiologically acceptable salts and esters thereof. These compounds can be used as medicaments.

20 Claims, No Drawings

METHYL-BENZIMIDAZOLE DERIVATIVES

PRIORITY TO RELATED APPLICATION(S)

This application is a divisional application of U.S. application Ser. No. 12/265,049, filed Nov. 5, 2008, which claims the benefit of European Patent Application No. 07120737.7, filed Nov. 15, 2007. The entire contents of the above-identified applications are hereby incorporated by reference.

BACKGROUND OF THE INVENTION

The Farnesoid-X-receptor (FXR) is a member of the nuclear hormone receptor superfamily of transcription factors. FXR was originally identified as a receptor activated by farnesol, and subsequent studies revealed a major role of FXR as a bile acid receptor [Makishima, M., Okamoto, A. Y., Repa, J. J., Tu, H., Learned, R. M., Luk, A., Hull, M. V., Lustig, K. D., Mangelsdorf, D. J. and Shan, B. Identification of a nuclear receptor for bile acids. *Science* 1999, 284, 1362-1365]. FXR is expressed in liver, intestine, kidney, and the adrenal gland. Four splice isoforms have been cloned in humans.

Among the major bile acids, chenodeoxycholic acid is the most potent FXR agonist. Binding of bile acids or synthetic ligands to FXR induces the transcriptional expression of small heterodimer partner (SHP), an atypical nuclear receptor family member that binds to several other nuclear hormone receptors, including LRH-1 and LXRalpha and blocks their transcriptional functions [Lu, T. T., Makishima, M., Repa, J. J., Schoonjans, K., Kerr, T. A., Auwerx, J. and Mangelsdorf, D. J. Molecular basis for feedback regulation of bile acid synthesis by nuclear receptors. *Mol. Cell* 2000, 6, 507-515]. CYP7A1 and CYP8B are enzymes involved in hepatic bile acid synthesis. FXR represses their expression via activation of the SHP pathway. FXR directly induces the expression of bile acid-exporting transporters for the ABC family in hepatocytes, including the bile salt export pump (ABCB11) and the multidrug resistance associated protein 2 (ABCC2) [Kast, H. R., Goodwin, B., Tan, P. T., Jones, S. A., Anisfeld, A. M., Stoltz, C. M., Tontonoz, P., Kliewer, S., Willson, T. M. and Edwards, P. A. Regulation of multidrug resistance-associated protein 2 (ABCC2) by the nuclear receptors pregnane X receptor, farnesoid X-activated receptor, and constitutive androstane receptor. *J. Biol. Chem.* 2002, 277, 2908-2915; Ananthanarayanan, M., Balasubramanian, N., Makishima, M., Mangelsdorf, D. J. and Suchy, F. J. Human bile salt export pump promoter is transactivated by the farnesoid X receptor/bile acid receptor. *J. Biol. Chem.* 2001, 276, 28857-28865]. FXR knockout mice have impaired resistance to bile acid-induced hepatotoxicity and synthetic FXR agonists have been shown to be hepatoprotective in animal models of cholestasis [Liu, Y., Binz, J., Numerick, M. J., Dennis, S., Luo, G., Desai, B., MacKenzie, K. I., Mansfield, T. A., Kliewer, S. A., Goodwin, B. and Jones, S. A. Hepatoprotection by the farnesoid X receptor agonist GW4064 in rat models of intra- and extra-hepatic cholestasis. *J. Clin. Invest.* 2003, 112, 1678-1687; Sinal, C. J., Tohkin, M., Miyata, M., Ward, J. M., Lambert, G. and Gonzalez, F. J. Targeted disruption of the nuclear receptor FXR/BAR impairs bile acid and lipid homeostasis. *Cell* 2000, 102, 731-744]. These data show that FXR protects hepatocytes from bile acid toxicity by suppressing both cellular synthesis and import of bile acids and stimulating their biliary excretion.

The process of enterohepatic circulation of bile acids is also a major regulator of serum cholesterol homeostasis. After biosynthesis from cholesterol in the liver, bile acids are secreted with bile into the lumen of the small intestine to aid in the digestion and absorption of fat and fat-soluble vitamins. The ratio of different bile acids determines their ability to solubilize cholesterol. FXR activation decreases the size and changes the composition of the bile acid pool, decreasing the intestinal solubilization of cholesterol, effectively blocking its absorption. Decreased absorption would be expected to result in lower plasma cholesterol levels. Indeed direct inhibitors of cholesterol absorption such as ezetimibe decrease plasma cholesterol, providing some evidence to support this hypothesis. However ezetimibe has limited efficacy which appears due to feedback upregulation of cholesterol synthesis in cells attempting to compensate for depletion of cholesterol. Recent data have shown that FXR opposes this effect in part by directly repressing the expression of HMGCoA reductase via a pathway involving SHP and LRH1 [Datta, S., Wang, L., Moore, D. D. and Osborne, T. F. Regulation of 3-hydroxy-3-methylglutaryl coenzyme A reductase promoter by nuclear receptors liver receptor homologue-1 and small heterodimer partner: a mechanism for differential regulation of cholesterol synthesis and uptake. *J. Biol. Chem.* 2006, 281, 807-812]. FXR also decreases hepatic synthesis of triglycerides by repressing SREBP1-c expression by an alternate pathway involving SHP and LXRalpha. Thus compounds that activate FXR may show superior therapeutic efficacy on plasma cholesterol and triglyceride lowering than current therapies.

Most patients with coronary artery disease have high plasma levels of atherogenic LDL. The HMGCoA reductase inhibitors (statins) are effective at normalizing LDL-C levels but reduce the risk for cardiovascular events such as stroke and myocardial infarction by only about 30%. Additional therapies targeting further lowering of atherogenic LDL as well as other lipid risk factors such as high plasma triglyceride levels and low HDL-C levels are needed.

A high proportion of type 2 diabetic patients in the United States have abnormal concentrations of plasma lipoproteins. The prevalence of total cholesterol>240 mg/dl is 37% in diabetic men and 44% in diabetic women and the prevalence for LDL-C>160 mg/dl are 31% and 44%, respectively in these populations. Diabetes is a disease in which a patient's ability to control glucose levels in blood is decreased because of partial impairment in the response to insulin. Type II diabetes (T2D), also called non-insulin dependent diabetes mellitus (NIDDM), accounts for 80-90% of all diabetes cases in developed countries. In T2D, the pancreatic Islets of Langerhans produce insulin but the primary target tissues (muscle, liver and adipose tissue) develop a profound resistance to its effects. The body compensates by producing more insulin ultimately resulting in failure of pancreatic insulin-producing capacity. Thus T2D is a cardiovascular-metabolic syndrome associated with multiple comorbidities including dyslipidemia and insulin resistance, as well as hypertension, endothelial dysfunction and inflammatory atherosclerosis.

The first line treatment for dyslipidemia and diabetes is a low-fat and low-glucose diet, exercise and weight loss. Compliance can be moderate and treatment of the various metabolic deficiencies that develop becomes necessary with, for example, lipid-modulating agents such as statins and fibrates, hypoglycemic drugs such as sulfonylureas and metformin, or insulin sensitizers of the thiazolidinedione (TZD) class of PPARgamma-agonists. Recent studies provide evidence that modulators of FXR may have enhanced therapeutic potential by providing superior normalization of both LDL-C and triglyceride levels, currently achieved only with combinations of existing drugs and, in addition, may avoid feedback effects on cellular cholesterol homeostasis.

The compounds of the present invention bind to and selectively modulate FXR very efficiently resulting in reducing cholesterol absorption, LDL lowering cholesterol and triglycerides, and lowering inflammatory atherosclerosis. Since multiple facets of combined dyslipidemia and cholesterol homeostasis are addressed by FXR modulators, they are expected to have an enhanced therapeutic potential compared to the compounds already known in the art.

SUMMARY OF THE INVENTION

The invention is concerned with novel methyl-benzimidazole derivatives of the formula (I)

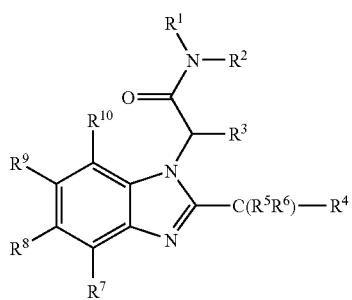

wherein
$R^1$ is cycloalkyl, lower-alkyl, cycloalkyl-lower-alkyl, aryl, aryl-lower-alkyl, heteroaryl, heteroaryl-lower-alkyl, heterocyclyl or heterocyclyl-lower-alkyl,
  wherein a cycloalkyl, aryl, heteroaryl or heterocyclyl can optionally be substituted with 1 to 4 substituents independently selected from the group consisting of hydroxy, halogen, lower-alkyl, lower-alkoxy, fluoro-lower-alkyl and fluoro-lower-alkoxy;
$R^2$ is hydrogen or lower-alkyl;
$R^3$ is cycloalkyl, lower-alkyl, cycloalkyl-lower-alkyl, aryl, heteroaryl-lower-alkyl, heterocyclyl or heterocyclyl-lower-alkyl,
  wherein a cycloalkyl, aryl, heteroaryl or heterocyclyl can optionally be substituted with 1 to 4 substituents independently selected from the group consisting of hydroxy, halogen, lower-alkyl, lower-alkoxy, fluoro-lower-alkyl, fluoro-lower-alkoxy and lower-alkoxy-carbonyl;
$R^4$ is aryl, cycloalkyl, heteroaryl or heterocyclyl,
  wherein aryl, cycloalkyl, heteroaryl or heterocyclyl can optionally be substituted with 1 to 4 substituents independently selected from the group consisting of halogen, lower-alkyl, lower-alkoxy, hydroxy, dioxo-lower-alkylene, fluoro-lower-alkyl and fluoro-lower-alkoxy;
$R^5$ and $R^6$ independently from each other are hydrogen, hydroxy, hydroxy-lower-alkyl, lower-alkoxy, lower-alkyl, fluoro-lower-alkyl or fluoro-lower-alkoxy;
$R^7$, $R^8$, $R^9$ and $R^{10}$ independently from each other are hydrogen, halogen, hydroxy, lower-alkyl, lower-alkoxy, fluoro-lower-alkyl or fluoro-lower-alkoxy;
and pharmaceutically acceptable salts and esters thereof.

Further, the invention is concerned with a process for the manufacture of the above compounds, pharmaceutical preparations which contain such compounds as well as the use of these compounds for the production of pharmaceutical preparations.

DETAILED DESCRIPTION OF THE INVENTION

A. Definitions

Unless otherwise indicated, the following definitions are set forth to illustrate and define the meaning and scope of the various terms used to describe the invention herein.

In this specification the term "lower" is used to mean a group consisting of one to seven, preferably of one to four carbon atom(s).

The term "halogen" refers to fluorine, chlorine, bromine and iodine, with fluorine, chlorine and bromine being preferred.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. Lower-alkyl groups as described below also are preferred alkyl groups.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like. Lower-alkyl groups can optionally be substituted, e.g., by hydroxy. Such substituted lower-alkyl-groups are referred to as "hydroxy-lower-alkyl". Unsubstituted lower-alkyl groups are preferred, unless stated otherwise.

The term "fluoro-lower-alkyl" refers to lower-alkyl groups which are mono- or multiply substituted with fluorine. Examples of fluoro-lower-alkyl groups are e.g., $CFH_2$, $CF_2H$, $CF_3$, $CF_3CH_2$, $CF_3(CH_2)_2$, $(CF_3)_2CH$ and $CF_2H$—$CF_2$.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substituents together forming a ring, such as, for example, —$NH_2$, methylamino, ethylamino, dimethylamino, diethylamino, methyl-ethylamino, pyrrolidin-1-yl or piperidino etc., preferably primary amino, dimethylamino and diethylamino and particularly dimethylamino. The term "formylamino" refers to the group HC(O)—N(H)—.

The term "cycloalkyl" refers to a monovalent carbocyclic radical of 3 to 10 carbon atoms, preferably 3 to 6 carbon atoms, such as cyclopropyl, cyclobutyl, cyclopentyl, or cyclohexyl. A cycloalkyl group can optionally be substituted as described in the description and claims.

The term "alkoxy" refers to the group R'—O—, wherein R' is an alkyl. The term "lower-alkoxy" refers to the group R'—O—, wherein R' is a lower-alkyl.

The term "fluoro-lower-alkoxy" refers to the group R"—O—, wherein R" is fluoro-lower-alkyl.

Examples of fluoro-lower-alkoxy groups are e.g., $CFH_2$—O, $CF_2H$—O, $CF_3$—O, $CF_3CH_2$—O, $CF_3(CH_2)_2$—O, $(CF_3)_2$ CH—O, and $CF_2H$—$CF_2$—O.

The term "alkylene" refers to a straight chain or branched divalent saturated aliphatic hydrocarbon group of 1 to 20 carbon atoms, preferably 1 to 16 carbon atoms, more preferably up to 10 carbon atoms. Lower-alkylene groups as described below also are preferred alkylene groups. The term "lower-alkylene" refers to a straight chain or branched divalent saturated aliphatic hydrocarbon group of 1 to 7, preferably 1 to 6 or 3 to 6 carbon atoms. Straight chain alkylene or lower-alkylene groups are preferred. The term "dioxo-lower-alkylene" refers to a group —O-lower-alkylene-O—.

The term "aryl", alone or in combination, relates to the phenyl or naphthyl group, preferably the phenyl group, which can optionally be substituted by 1 to 5, preferably 1 to 3, substituents independently selected from the group consisting of lower-alkyl, lower-alkoxy, dioxo-lower-alkylene (forming e.g. a benzodioxolyl group), halogen, hydroxy, CN, $CF_3$, amino, aminocarbonyl, carboxy, $NO_2$, lower-alkylsulfonyl, aminosulfonyl, lower-alkylcarbonyl, lower-alkylcarbonyloxy, lower-alkylcarbonyl-N(H), lower-alkyl-carbonyl-N(lower-alkyl), lower-alkoxycarbonyl, fluoro-lower-alkyl, fluoro-lower-alkoxy, cycloalkyl, phenyloxy, methyl-oxadiazolyl, morpholinyl, formylamino. Preferred substituents are halogen, lower-alkyl, fluoro-lower-alkyl and CN. Furthermore, aryl groups may preferably be substituted as described in the description and claims below.

The term "heteroaryl" refers to an aromatic 5 to 6 membered monocyclic ring or 9 to 10 membered bicyclic ring which can comprise 1, 2 or 3 atoms selected from nitrogen, oxygen and/or sulphur, such as furyl, pyridinyl, 2-oxo-1,2-dihydro-pyridinyl, pyridazinyl, pyrimidinyl, pyrazinyl, thiophenyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzodioxolyl, benzoimidazolyl, indolyl, isoindolyl, 1,3-dioxo-isoindolyl, quinolinyl, indazolyl, benzoisothiazolyl, benzoxazolyl and benzoisoxazolyl. A preferred heteroaryl group is e.g. pyridinyl. A heteroaryl group may have a substitution pattern as described earlier in connection with the term "aryl". Furthermore, a heteroaryl group may preferably be substituted as described in the description and claims below.

The term "heterocyclyl" refers to 5 to 6 membered monocyclic ring or 8 to 10 membered bi- or tricyclic ring which can comprise 1, 2 or 3 atoms selected from nitrogen, oxygen and/or sulphur, such as morpholinyl, thiomorpholinyl, tetrahydropyranyl, 1,1-dioxo-thiomorpholinyl, piperidinyl, 2-oxo-piperidinyl, pyrrolidinyl, 2-oxo-pyrrolidinyl, piperazin-2-one, 8-oxa-3-aza-bicyclo[3.2.1]octyl and piperazinyl. A heterocyclyl may optionally have a substitution pattern as described earlier in connection with the term "aryl". Furthermore, a heterocyclyl group may preferably be substituted as described in the description and claims below.

The term "protecting group" refers to groups which are used to protect functional groups, particularly hydroxy groups, temporarily. Examples of protecting groups are benzyl, p-methoxybenzyl, t-butyl-dimethylsilyl, t-butyl-diphenylsilyl and (for protection of amino groups) Boc and benzyloxycarbonyl.

Compounds of formula (I) can form pharmaceutically acceptable acid addition salts. Examples of such pharmaceutically acceptable salts are salts of compounds of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula (I) in which an acidic group is present can further form salts with bases. Examples of such salts are alkaline, earth-alkaline and ammonium salts such as e.g., Na—, K—, Ca— and trimethylammoniumsalt. The term "pharmaceutically acceptable salts" also refers to such salts. Salts obtained by the addition of an acid are preferred.

The term "pharmaceutically acceptable esters" embraces derivatives of the compounds of formula (I), in which a carboxy group has been converted to an ester. Lower-alkyl, hydroxy-lower-alkyl, lower-alkoxy-lower-alkyl, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aralkyl esters are examples of suitable esters. The methyl, ethyl, propyl, butyl and benzyl esters are preferred esters. The methyl and ethyl esters are especially preferred. The term "pharmaceutically acceptable esters" furthermore embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

All references herein recited are hereby incorporated by reference in their entirety.

B. DETAILED DESCRIPTION OF THE INVENTION

In detail, the present invention relates to compounds of formula (I)

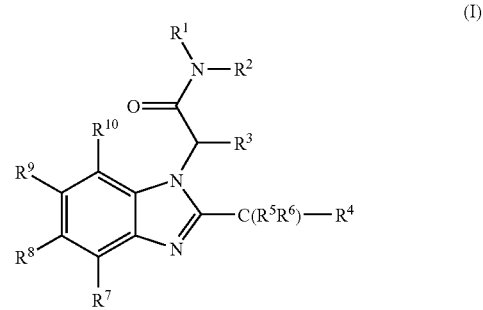

(I)

wherein
$R^1$ is cycloalkyl, lower-alkyl, cycloalkyl-lower-alkyl, aryl, aryl-lower-alkyl, heteroaryl, heteroaryl-lower-alkyl, heterocyclyl or heterocyclyl-lower-alkyl,
  wherein a cycloalkyl, aryl, heteroaryl or heterocyclyl can optionally be substituted with 1 to 4 substituents independently selected from the group consisting of hydroxy, halogen, lower-alkyl, lower-alkoxy, fluoro-lower-alkyl and fluoro-lower-alkoxy;
$R^2$ is hydrogen or lower-alkyl;
$R^3$ is cycloalkyl, lower-alkyl, cycloalkyl-lower-alkyl, aryl, heteroaryl-lower-alkyl, heterocyclyl or heterocyclyl-lower-alkyl,
  wherein a cycloalkyl, aryl, heteroaryl or heterocyclyl can optionally be substituted with 1 to 4 substituents independently selected from the group consisting of hydroxy, halogen, lower-alkyl, lower-alkoxy, fluoro-lower-alkyl, fluoro-lower-alkoxy and lower-alkoxy-carbonyl;
$R^4$ is aryl, cycloalkyl, heteroaryl or heterocyclyl,
  wherein aryl, cycloalkyl, heteroaryl or heterocyclyl can optionally be substituted with 1 to 4 substituents independently selected from the group consisting of halogen, lower-alkyl, lower-alkoxy, hydroxy, dioxo-lower-alkylene, fluoro-lower-alkyl and fluoro-lower-alkoxy;
$R^5$ and $R^6$ independently from each other are hydrogen, hydroxy, hydroxy-lower-alkyl, lower-alkoxy, lower-alkyl, fluoro-lower-alkyl or fluoro-lower-alkoxy;

$R^7$, $R^8$, $R^9$ and $R^{10}$ independently from each other are hydrogen, halogen, hydroxy, lower-alkyl, lower-alkoxy, fluoro-lower-alkyl or fluoro-lower-alkoxy;

and pharmaceutically acceptable salts and esters thereof.

Compounds of formula (I) are individually preferred and physiologically acceptable salts thereof are individually preferred and pharmaceutically acceptable esters thereof are individually preferred, with the compounds of formula (I) being particularly preferred.

The compounds of formula (I) have one or more asymmetric C atoms and can therefore exist as an enantiomeric mixture, diastereomeric mixture or as optically pure compounds.

Preferred are compounds of formula (I), wherein $R^3$ is cycloalkyl, lower-alkyl, cycloalkyl-lower-alkyl, aryl, heteroaryl-lower-alkyl, heterocyclyl or heterocyclyl-lower-alkyl, wherein a cycloalkyl, aryl, heteroaryl or heterocyclyl can optionally be substituted with 1 to 4 substituents independently selected from the group consisting of hydroxy, halogen, lower-alkyl, lower-alkoxy, fluoro-lower-alkyl and fluoro-lower-alkoxy.

Preferred compounds of formula (I) as described above are those, wherein $R^1$ is cycloalkyl or aryl, which aryl can optionally be substituted with hydroxy. More preferably, $R^1$ is cyclopentyl, cyclohexyl or 4-hydroxy-phenyl.

Other preferred compounds are those, wherein $R^2$ is hydrogen. Furthermore, it is preferred that $R^3$ is cycloalkyl, particularly that $R^3$ is cyclohexyl.

Furthermore, preferred compounds of formula (I) are those wherein $R^3$ is cyclohexyl, ethoxy-phenyl, chloro-phenyl, benyzodioxolyl, chloro-benyzodioxolyl, tetrahydro-thiopyranyl, tetrahydro-thiopyranyl-methyl, dioxo-hexahydro-thiopyranyl, dioxo-hexahydro-thiopyranyl-methyl, chlorophenyl or ethoxy-carboxy-cyclopropyl.

Another preferred embodiment of the present invention relates to compounds of formula (I) as defined above, wherein $R^4$ is aryl or pyridinyl, which aryl can optionally be substituted with 1 to 3 substituents independently selected from the group consisting of halogen, lower-alkyl, lower-alkoxy, hydroxy and dioxo-lower-alkylene. Examples of phenyl which is substituted with dioxo-lower-alkylene are e.g. benzodioxolyl groups, particularly benzo[1,3]dioxol-5-yl. Preferably, $R^4$ is phenyl which can optionally be substituted with 1 to 2 substituents independently selected from the group consisting of halogen, lower-alkoxy and dioxo-lower-alkylene. More preferably, $R^4$ is 3-chloro-phenyl, 3-methoxy-phenyl, 2,4-difluoro-phenyl, phenyl, benzo[1,3]dioxol-5-yl or 3,5-difluoro-phenyl.

Furthermore, preferred compounds of formula (I) are those, wherein $R^5$ and $R^6$ independently from each other are hydrogen, hydroxy, hydroxy-lower-alkyl, lower-alkoxy or lower-alkyl.

Preferably, $R^5$ is hydrogen or lower-alkoxy. More preferably, $R^5$ is hydrogen or methoxy.

Preferably, $R^6$ is hydrogen or lower-alkyl. More preferably, $R^6$ is hydrogen.

Another preferred embodiment of the present invention relates to compounds of formula (I) as described above, wherein $R^7$, $R^8$, $R^9$ and $R^{10}$ independently from each other are hydrogen or halogen. Preferably, $R^7$ is hydrogen. Preferably, $R^8$ is halogen, more preferably $R^8$ is fluoro. Preferably, $R^9$ is hydrogen or halogen, more preferably $R^9$ is hydrogen or fluoro. Preferably, $R^{10}$ is hydrogen.

In particular, preferred compounds are the compounds of formula (I) described in the examples as individual compounds as well as pharmaceutically acceptable salts as well as pharmaceutically acceptable esters thereof.

Preferred compounds of formula (I) are those selected from the group consisting of:

2-[2-(3-Chloro-benzyl)-5,6-difluoro-benzoimidazol-1-yl]-2,N-dicyclohexyl-acetamide, 2,N-Dicyclohexyl-2-[5,6-difluoro-2-(4-isopropyl-benzyl)-benzoimidazol-1-yl]-acetamide, 2,N-Dicyclohexyl-2-[2-(4-ethoxy-benzyl)-5,6-difluoro-benzoimidazol-1-yl]-acetamide, 2,N-Dicyclohexyl-2-[5,6-difluoro-2-(3-methoxy-benzyl)-benzoimidazol-1-yl]-acetamide, 2,N-Dicyclohexyl-2-[2-(3,4-dimethoxy-benzyl)-5,6-difluoro-benzoimidazol-1-yl]-acetamide, 2,N-Dicyclohexyl-2-[5,6-difluoro-2-(2-hydroxy-benzyl)-benzoimidazol-1-yl]-acetamide, 2,N-Dicyclohexyl-2-[2-(2,4-difluoro-benzyl)-5,6-difluoro-benzoimidazol-1-yl]-acetamide, 2-{2-[(4-Chloro-phenyl)-hydroxy-methyl]-5,6-difluoro-benzoimidazol-1-yl}-2,N-dicyclohexyl-acetamide, 2-{2-[(R)-(4-Chloro-phenyl)-hydroxy-methyl]-5,6-difluoro-benzoimidazol-1-yl}-2,N-dicyclohexyl-acetamide, 2,N-Dicyclohexyl-2-[5,6-difluoro-2-((S)-hydroxy-phenyl-methyl)-benzoimidazol-1-yl]-acetamide, (+)-2,N-Dicyclohexyl-2-[5,6-difluoro-2-((R)-hydroxy-phenyl-methyl)-benzoimidazol-1-yl]-acetamide, 2,N-Dicyclohexyl-2-[5,6-difluoro-2-((S)-hydroxy-phenyl-methyl)-benzoimidazol-1-yl]-acetamide, 2-{2-[(R)-(3-Chloro-phenyl)-hydroxy-methyl]-5,6-difluoro-benzoimidazol-1-yl}-2,N-dicyclohexyl-acetamide, 2-{2-[(S)-(3-Chloro-phenyl)-hydroxy-methyl]-5,6-difluoro-benzoimidazol-1-yl}-2,N-dicyclohexyl-acetamide, 2,N-Dicyclohexyl-2-{2-[(R)-(3,4-dichloro-phenyl)-hydroxy-methyl]-5,6-difluoro-benzoimidazol-1-yl}-acetamide, 2,N-Dicyclohexyl-2-{2-[(2,3-dichloro-phenyl)-hydroxy-methyl]-5,6-difluoro-benzoimidazol-1-yl}-acetamide, 2,N-Dicyclohexyl-2-[5,6-difluoro-2-(hydroxy-pyridin-2-yl-methyl)-benzoimidazol-1-yl]-acetamide, 2,N-Dicyclohexyl-2-[5,6-difluoro-2-(hydroxy-pyridin-3-yl-methyl)-benzoimidazol-1-yl]-acetamide, 2,N-Dicyclohexyl-2-{2-[1-(3,4-dichloro-phenyl)-1-hydroxy-ethyl]-5,6-difluoro-benzoimidazol-1-yl}-acetamide, 2,N-Dicyclohexyl-2-[5,6-difluoro-2-(1-hydroxy-1-pyridin-2-yl-ethyl)-benzoimidazol-1-yl]-acetamide, 2,N-Dicyclohexyl-2-[5,6-difluoro-2-(methoxy-phenyl-methyl)-benzoimidazol-1-yl]-acetamide, 2,N-Dicyclohexyl-2-[5,6-difluoro-2-((R)-methoxy-phenyl-methyl)-benzoimidazol-1-yl]-acetamide, (−)-2,N-Dicyclohexyl-2-[5,6-difluoro-2-((R)-methoxy-phenyl-methyl)-benzoimidazol-1-yl]-acetamide, (+)-2-Cyclohexyl-N-cyclopentyl-2-[5,6-difluoro-2-((R)-methoxy-phenyl-methyl)-benzoimidazol-1-yl]-acetamide, (−)-(S)-2,N-Dicyclohexyl-2-[5,6-difluoro-2-((S)-methoxy-phenyl-methyl)-benzoimidazol-1-yl]-acetamide, (−)-(R)-2,N-Dicyclohexyl-2-[5,6-difluoro-2-((S)-methoxy-phenyl-methyl)-benzoimidazol-1-yl]-acetamide, (−)-(S)-2-Cyclohexyl-N-cyclopentyl-2-[5,6-difluoro-2-((S)-methoxy-phenyl-methyl)-benzoimidazol-1-yl]-acetamide, (+)-(R)-2-Cyclohexyl-N-cyclopentyl-2-[5,6-difluoro-2-((S)-methoxy-phenyl-methyl)-benzoimidazol-1-yl]-acetamide, 2-[2-(Benzo[1,3]dioxol-5-yl-methoxy-methyl)-5,6-difluoro-benzoimidazol-1-yl]-2,N-dicyclohexyl-acetamide, (−)-2-[2-(Benzo[1,3]dioxol-5-yl-methoxy-methyl)-5,6-difluoro-benzoimidazol-1-yl]-2,N-dicyclohexyl-acetamide, (+)-2-[2-(Benzo[1,3]dioxol-5-yl-methoxy-methyl)-5,6-difluoro-benzoimidazol-1-yl]-2,N-dicyclohexyl-acetamide,
2,N-Dicyclohexyl-2-{5,6-difluoro-2-[(2-fluoro-5-methoxy-phenyl)-methoxy-methyl]-benzoimidazol-1-yl}-acetamide,
2,N-Dicyclohexyl-2-{5,6-difluoro-2-[(2-fluoro-4-methoxy-phenyl)-methoxy-methyl]-benzoimidazol-1-yl}-acetamide,
2,N-Dicyclohexyl-2-{2-[(3,5-difluoro-phenyl)-methoxy-methyl]-5,6-difluoro-benzoimidazol-1-yl}-acetamide,
2,N-Dicyclohexyl-2-{2-[(4-ethoxy-2,6-difluoro-phenyl)-methoxy-methyl]-5,6-difluoro-benzoimidazol-1-yl}-acetamide,
2,N-Dicyclohexyl-2-{2-[(2,6-difluoro-phenyl)-methoxy-methyl]-5,6-difluoro-benzoimidazol-1-yl}-acetamide,
2,N-Dicyclohexyl-2-{2-[(2,3-difluoro-phenyl)-methoxy-methyl]-5,6-difluoro-benzoimidazol-1-yl}-acetamide,
2,N-Dicyclohexyl-2-[5,6-difluoro-2-(2-hydroxy-1-phenyl-ethyl)-benzoimidazol-1-yl]-acetamide,
2-[2-(3-Chloro-benzyl)-5-fluoro-benzoimidazol-1-yl]-2,N-dicyclohexyl-acetamide,
2,N-Dicyclohexyl-2-[5-fluoro-2-(4-isopropyl-benzyl)-benzoimidazol-1-yl]-acetamide,
2,N-Dicyclohexyl-2-[2-(4-ethoxy-benzyl)-5-fluoro-benzoimidazol-1-yl]-acetamide,
2,N-Dicyclohexyl-2-[5-fluoro-2-(3-methoxy-benzyl)-benzoimidazol-1-yl]-acetamide,
2,N-Dicyclohexyl-2-[2-(3,4-dimethoxy-benzyl)-5-fluoro-benzoimidazol-1-yl]-acetamide,
2,N-Dicyclohexyl-2-[2-(2,4-difluoro-benzyl)-5-fluoro-benzoimidazol-1-yl]-acetamide,
2-{2-[(4-Chloro-phenyl)-hydroxy-methyl]-5-fluoro-benzoimidazol-1-yl}-2,N-dicyclohexyl-acetamide,
2,N-Dicyclohexyl-2-[5-fluoro-2-(methoxy-phenyl-methyl)-benzoimidazol-1-yl]-acetamide,
2-(2-Benzyl-6-chloro-5-fluoro-benzoimidazol-1-yl)-2,N-dicyclohexyl-acetamide,
2-[6-Chloro-5-fluoro-2-(hydroxy-phenyl-methyl)-benzoimidazol-1-yl]-2,N-dicyclohexyl-acetamide,
2-(2-Benzyl-benzoimidazol-1-yl)-2,N-dicyclohexyl-acetamide,
2-Cyclohexyl-2-[5-fluoro-2-((R)-methoxy-phenyl-methyl)-benzoimidazol-1-yl]-N-(4-hydroxy-cyclohexyl)-acetamide,
2-Cyclohexyl-2-[5-fluoro-2-((R)-methoxy-phenyl-methyl)-benzoimidazol-1-yl]-N-(4-hydroxy-cyclohexyl)-acetamide, and
2-Cyclohexyl-N-cyclopentyl-2-[5-fluoro-2-((R)-methoxy-phenyl-methyl)-benzoimidazol-1-yl]-acetamide, Further preferred compounds of formula (I) are those selected from the group consisting of
2-Cyclohexyl-2-[5,6-difluoro-2-((R)-methoxy-phenyl-methyl)-benzoimidazol-1-yl]-N-(4-hydroxy-cyclohexyl)-acetamide,
N-Cyclohexyl-2-[5,6-difluoro-2-(methoxy-phenyl-methyl)-benzoimidazol-1-yl]-2-(4-methoxy-phenyl)-acetamide,
2-Benzo[1,3]dioxol-5-yl-N-cyclohexyl-2-[5,6-difluoro-2-(methoxy-phenyl-methyl)-benzoimidazol-1-yl]-acetamide,
N-Cyclohexyl-2-[5,6-difluoro-2-(methoxy-phenyl-methyl)-benzoimidazol-1-yl]-3-(tetrahydro-thiopyran-4-yl)-propionamide,
2-(3-Chloro-phenyl)-N-cyclohexyl-2-[5,6-difluoro-2-(methoxy-phenyl-methyl)-benzoimidazol-1-yl]-acetamide,
N-Cyclohexyl-2-[2-(cyclohexyl-methoxy-methyl)-5,6-difluoro-benzoimidazol-1-yl]-2-(4-methoxy-phenyl)-acetamide,
2-Benzo[1,3]dioxol-5-yl-N-cyclohexyl-2-[2-(cyclohexyl-methoxy-methyl)-5,6-difluoro-benzoimidazol-1-yl]-acetamide,
N-Cyclohexyl-2-[2-(cyclohexyl-methoxy-methyl)-5,6-difluoro-benzoimidazol-1-yl]-3-(tetrahydro-thiopyran-4-yl)-propionamide,
2-(3-Chloro-phenyl)-N-cyclohexyl-2-[2-(cyclohexyl-methoxy-methyl)-5,6-difluoro-benzoimidazol-1-yl]-acetamide,
N-Cyclopentyl-2-[5,6-difluoro-2-(methoxy-phenyl-methyl)-benzoimidazol-1-yl]-2-(4-methoxy-phenyl)-acetamide,
2-Benzo[1,3]dioxol-5-yl-N-cyclopentyl-2-[5,6-difluoro-2-(methoxy-phenyl-methyl)-benzoimidazol-1-yl]-acetamide,
N-Cyclopentyl-2-[5,6-difluoro-2-(methoxy-phenyl-methyl)-benzoimidazol-1-yl]-3-(tetrahydro-thiopyran-4-yl)-propionamide,
2-(3-Chloro-phenyl)-N-cyclopentyl-2-[5,6-difluoro-2-(methoxy-phenyl-methyl)-benzoimidazol-1-yl]-acetamide,
2-[2-(Cyclohexyl-methoxy-methyl)-5,6-difluoro-benzoimidazol-1-yl]-N-cyclopentyl-2-(4-methoxy-phenyl)-acetamide,
2-Benzo[1,3]dioxol-5-yl-2-[2-(cyclohexyl-methoxy-methyl)-5,6-difluoro-benzoimidazol-1-yl]-N-cyclopentyl-acetamide,
2-[2-(Cyclohexyl-methoxy-methyl)-5,6-difluoro-benzoimidazol-1-yl]-N-cyclopentyl-3-(tetrahydro-thiopyran-4-yl)-propionamide,
2-(3-Chloro-phenyl)-2-[2-(cyclohexyl-methoxy-methyl)-5,6-difluoro-benzoimidazol-1-yl]-N-cyclopentyl-acetamide,
2-[6-Chloro-5-fluoro-2-(methoxy-phenyl-methyl)-benzoimidazol-1-yl]-N-cyclohexyl-2-(4-methoxy-phenyl)-acetamide,
2-(6-Chloro-benzo[1,3]dioxol-5-yl)-2-[6-chloro-5-fluoro-2-(methoxy-phenyl-methyl)-benzoimidazol-1-yl]-N-cyclohexyl-acetamide,
2-[6-Chloro-5-fluoro-2-(methoxy-phenyl-methyl)-benzoimidazol-1-yl]-N-cyclohexyl-3-(tetrahydro-thiopyran-4-yl)-propionamide,
2-[6-Chloro-5-fluoro-2-(methoxy-phenyl-methyl)-benzoimidazol-1-yl]-2-(3-chloro-phenyl)-N-cyclohexyl-acetamide,
2-[6-Chloro-2-(cyclohexyl-methoxy-methyl)-5-fluoro-benzoimidazol-1-yl]-N-cyclohexyl-2-(4-methoxy-phenyl)-acetamide,
2-Benzo[1,3]dioxol-5-yl-2-[6-chloro-2-(cyclohexyl-methoxy-methyl)-5-fluoro-benzoimidazol-1-yl]-N-cyclohexyl-acetamide,
2-(6-Chloro-benzo[1,3]dioxol-5-yl)-2-[6-chloro-2-(cyclohexyl-methoxy-methyl)-5-fluoro-benzoimidazol-1-yl]-N-cyclohexyl-acetamide,
2-[6-Chloro-2-(cyclohexyl-methoxy-methyl)-5-fluoro-benzoimidazol-1-yl]-2-(3-chloro-phenyl)-N-cyclohexyl-acetamide,
2-[6-Chloro-5-fluoro-2-(methoxy-phenyl-methyl)-benzoimidazol-1-yl]-N-cyclopentyl-2-(4-methoxy-phenyl)-acetamide,
2-(6-Chloro-benzo[1,3]dioxol-5-yl)-2-[6-chloro-5-fluoro-2-(methoxy-phenyl-methyl)-benzoimidazol-1-yl]-N-cyclopentyl-acetamide, 2-[6-Chloro-5-fluoro-2-(methoxy-phenyl-methyl)-benzoimidazol-1-yl]-N-cyclopentyl-3-(tetrahydro-thiopyran-4-yl)-propionamide,
2-[6-Chloro-5-fluoro-2-(methoxy-phenyl-methyl)-benzoimidazol-1-yl]-2-(3-chloro-phenyl)-N-cyclopentyl-acetamide,
2-[6-Chloro-2-(cyclohexyl-methoxy-methyl)-5-fluoro-benzoimidazol-1-yl]-N-cyclopentyl-2-(4-methoxy-phenyl)-acetamide,
2-Benzo[1,3]dioxol-5-yl-2-[6-chloro-2-(cyclohexyl-methoxy-methyl)-5-fluoro-benzoimidazol-1-yl]-N-cyclopentyl-acetamide,
2-[6-Chloro-2-(cyclohexyl-methoxy-methyl)-5-fluoro-benzoimidazol-1-yl]-N-cyclopentyl-3-(tetrahydro-thiopyran-4-yl)-propionamide,
2-[6-Chloro-2-(cyclohexyl-methoxy-methyl)-5-fluoro-benzoimidazol-1-yl]-2-(3-chloro-phenyl)-N-cyclopentyl-acetamide,
2,N-Dicyclohexyl-2-[2-(cyclohexyl-methoxy-methyl)-5,6-difluoro-benzoimidazol-1-yl]-acetamide,
N-Cyclohexyl-2-[5,6-difluoro-2-((R)-2,2,2-trifluoro-1-methoxy-1-phenyl-ethyl)-benzoimidazol-1-yl]-2-(4-methoxy-phenyl)-acetamide,
N-Cyclohexyl-2-[5,6-difluoro-2-((S)-2,2,2-trifluoro-1-methoxy-1-phenyl-ethyl)-benzoimidazol-1-yl]-2-(4-methoxy-phenyl)-acetamide,
2-[2-(Benzo[1,3]dioxol-5-yl-methoxy-methyl)-5,6-difluoro-benzoimidazol-1-yl]-N-cyclohexyl-2-(4-methoxy-phenyl)-acetamide,
2-Cyclohexyl-2-[2-(cyclohexyl-methoxy-methyl)-5,6-difluoro-benzoimidazol-1-yl]-N-cyclopentyl-acetamide,
N-Cyclopentyl-2-[5,6-difluoro-2-((S)-2,2,2-trifluoro-1-methoxy-1-phenyl-ethyl)-benzoimidazol-1-yl]-2-(4-methoxy-phenyl)-acetamide,
2-[2-(Benzo[1,3]dioxol-5-yl-methoxy-methyl)-5,6-difluoro-benzoimidazol-1-yl]-N-cyclopentyl-2-(4-methoxy-phenyl)-acetamide,
N-Cyclohexyl-2-[5,6-difluoro-2-((S)-methoxy-phenyl-methyl)-benzoimidazol-1-yl]-2-(tetrahydro-thiopyran-4-yl)-acetamide,
N-Cyclohexyl-2-[5,6-difluoro-2-((S)-methoxy-phenyl-methyl)-benzoimidazol-1-yl]-3-(tetrahydro-thiopyran-4-yl)-propionamide,
2-{Cyclohexylcarbamoyl-[5,6-difluoro-2-((S)-methoxy-phenyl-methyl)-benzoimidazol-1-yl]-methyl}-cyclopropanecarboxylic acid ethyl ester,
N-Cyclohexyl-2-[5,6-difluoro-2-((R)-methoxy-phenyl-methyl)-benzoimidazol-1-yl]-2-(tetrahydro-thiopyran-4-yl)-acetamide,
N-Cyclohexyl-2-[5,6-difluoro-2-((R)-methoxy-phenyl-methyl)-benzoimidazol-1-yl]-3-(tetrahydro-thiopyran-4-yl)-propionamide,
2-{Cyclohexylcarbamoyl-[5,6-difluoro-2-((R)-methoxy-phenyl-methyl)-benzoimidazol-1-yl]-methyl}-cyclopropanecarboxylic acid ethyl ester,
N-Cyclohexyl-2-[5,6-difluoro-2-((S)-methoxy-phenyl-methyl)-benzoimidazol-1-yl]-2-(1,1-dioxo-hexahydro-1,6-thiopyran-4-yl)-acetamide,
N-Cyclohexyl-2-[5,6-difluoro-2-((R)-methoxy-phenyl-methyl)-benzoimidazol-1-yl]-2-(1,1-dioxo-hexahydro-1,6-thiopyran-4-yl)-acetamide,
N-Cyclohexyl-2-[5,6-difluoro-2-((R)-methoxy-phenyl-methyl)-benzoimidazol-1-yl]-3-(1,1-dioxo-hexahydro-1,6-thiopyran-4-yl)-propionamide,
and pharmaceutically acceptable salts and esters thereof.

Particularly preferred compounds of formula (I) are those selected from the group consisting of
2,N-Dicyclohexyl-2-[5,6-difluoro-2-(3-methoxy-benzyl)-benzoimidazol-1-yl]-acetamide,
2,N-Dicyclohexyl-2-[2-(2,4-difluoro-benzyl)-5,6-difluoro-benzoimidazol-1-yl]-acetamide,
2,N-Dicyclohexyl-2-[5,6-difluoro-2-(methoxy-phenyl-methyl)-benzoimidazol-1-yl]-acetamide,
(–)-2,N-Dicyclohexyl-2-[5,6-difluoro-2-((R)-methoxy-phenyl-methyl)-benzoimidazol-1-yl]-acetamide,
(–)-(S)-2-Cyclohexyl-N-cyclopentyl-2-[5,6-difluoro-2-((S)-methoxy-phenyl-methyl)-benzoimidazol-1-yl]-acetamide,
(–)-2-[2-(Benzo[1,3]dioxol-5-yl-methoxy-methyl)-5,6-difluoro-benzoimidazol-1-yl]-2,N-dicyclohexyl-acetamide,
2,N-Dicyclohexyl-2-{2-[(3,5-difluoro-phenyl)-methoxy-methyl]-5,6-difluoro-benzoimidazol-1-yl}-acetamide,
2-[2-(3-Chloro-benzyl)-5-fluoro-benzoimidazol-1-yl]-2,N-dicyclohexyl-acetamide,
2,N-Dicyclohexyl-2-[5-fluoro-2-(methoxy-phenyl-methyl)-benzoimidazol-1-yl]-acetamide,
2-Cyclohexyl-2-[5-fluoro-2-((R)-methoxy-phenyl-methyl)-benzoimidazol-1-yl]-N-(4-hydroxy-cyclohexyl)-acetamide, and
2-Cyclohexyl-N-cyclopentyl-2-[5-fluoro-2-((R)-methoxy-phenyl-methyl)-benzoimidazol-1-yl]-acetamide,
and pharmaceutically acceptable salts and esters thereof.

Also particularly preferred compounds of formula (I) are those selected from the group consisting of
2-Cyclohexyl-2-[5,6-difluoro-2-((R)-methoxy-phenyl-methyl)-benzoimidazol-1-yl]-N-(4-hydroxy-cyclohexyl)-acetamide,
2-(3-Chloro-phenyl)-N-cyclohexyl-2-[5,6-difluoro-2-(methoxy-phenyl-methyl)-benzoimidazol-1-yl]-acetamide,
2-(3-Chloro-phenyl)-N-cyclopentyl-2-[5,6-difluoro-2-(methoxy-phenyl-methyl)-benzoimidazol-1-yl]-acetamide,
2-(3-Chloro-phenyl)-2-[2-(cyclohexyl-methoxy-methyl)-5,6-difluoro-benzoimidazol-1-yl]-N-cyclopentyl-acetamide,
2-[6-Chloro-5-fluoro-2-(methoxy-phenyl-methyl)-benzoimidazol-1-yl]-2-(3-chloro-phenyl)-N-cyclohexyl-acetamide,
2,N-Dicyclohexyl-2-[2-(cyclohexyl-methoxy-methyl)-5,6-difluoro-benzoimidazol-1-yl]-acetamide,
N-Cyclohexyl-2-[5,6-difluoro-2-((R)-methoxy-phenyl-methyl)-benzoimidazol-1-yl]-2-(tetrahydro-thiopyran-4-yl)-acetamide,
and pharmaceutically acceptable salts and esters thereof.

It will be appreciated that the compounds of general formula (I) in this invention may be derivatised at functional groups to provide derivatives which are capable of conversion back to the parent compound in vivo.

The invention further relates to a process for the manufacture of compounds of formula (I) as defined above, which process comprises a) cyclization of a compound of formula (II)

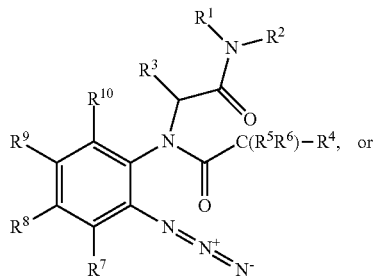

b) cyclization of a compound of formula (III)

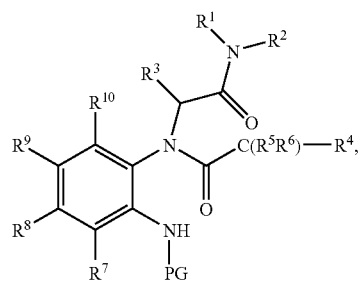

wherein $R^1$, $R^2$, $R^3$, $R^4$, $R^5$, $R^6$, $R^7$, $R^8$, $R^9$ and $R^{10}$ are as defined above and PG is a protecting group.

The cyclization of a compound of formula (II) or formula (III) can be performed under reaction conditions well known to the person skilled in the art, e.g., by the methods described below and in analogy to the examples described below. Suitable protecting groups in compounds of formula (III) are e.g., tert-butyloxycarbonyl (tert-BOC) and benzyloxycarbonyl.

The present invention also relates to compounds of formula (I) as defined above, when prepared by a process as described above.

The compounds of formula (I) as well as the starting materials of formula (II) and (III) can be prepared by methods known in the art or as described below. Unless otherwise indicated, the substituents $R^1$, $R^2$, $R^3$, $R^4$, $R^5$, $R^6$, $R^7$, $R^8$, $R^9$ and $R^{10}$ are as described above.

Compounds of formula (I) according to the present invention can be prepared e.g., by the methods and procedures given below. A typical procedure for the preparation of compounds of formula I is illustrated in Scheme 1.

Scheme 1

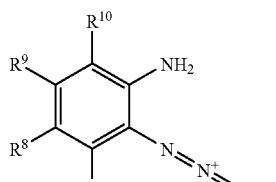

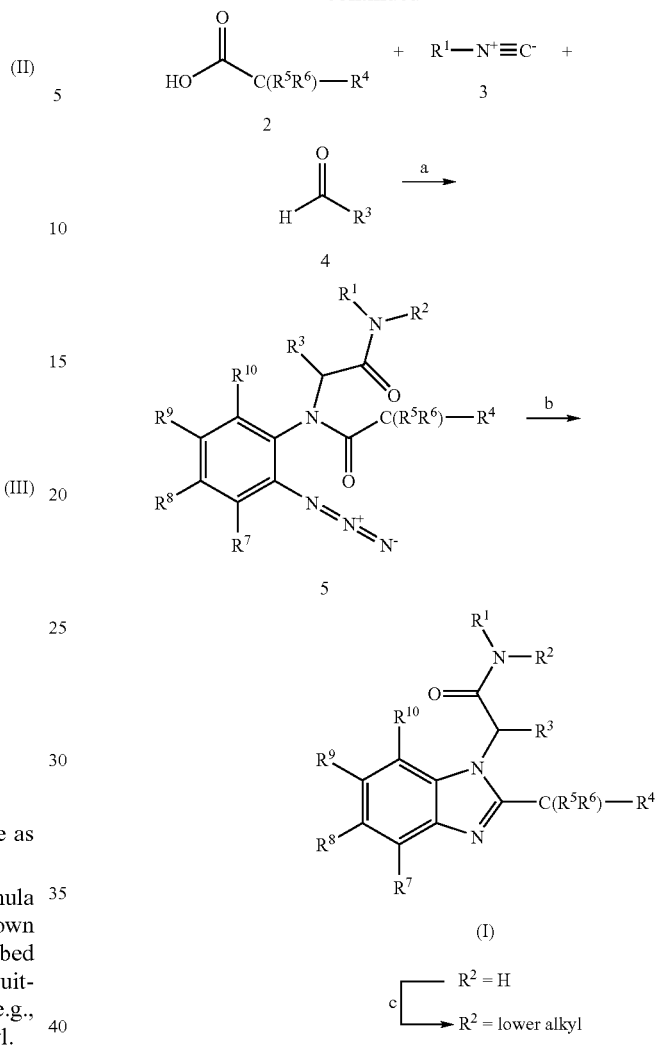

In a suitable organic solvent such as e.g., methanol a 2-azidoarylamine 1, a carboxylic acid 2, an isonitrile 3 and an aldehyde 4 are condensed to 5 in a multi-component reaction (MCR), a so called Ugi-type reaction (Scheme 1, step a; typical procedures may e.g., be found in "The Peptides" by Gross & Meienhofer Vol. 2, Academic Press, N.Y., 1980, pp 365-381). In a subsequent intramolecular Staudinger-type reaction with a suitable reagent such as e.g., $PPh_3$, the azido bisamide 5 is converted to the benzimidazole I (Scheme 1, step b), which can be optionally N-alkylated by deprotonation with a strong base (e.g., NaH or LiHMDA) and subsequent treatment with an alkylating agent $R^2$—X with X being a typical leaving group such as e.g., Cl, Br, I, $SO_2$alkyl, $SO_2$fluoroalkyl, $SO_2$aryl (Scheme 1, step c). Many of the building blocks 2-4, particularly the carboxylic acids 2, are commercially available. If not, they may be prepared from commercially available starting materials using procedures described in literature and typically known to those skilled in the art. For instance, -alkoxyaryl acetic acids 2 can be synthesized by base-catalyzed condensation of aldehydes 6 with haloforms (e.g., chloroform) and alcohols (e.g., methanol) as described by W. Reeve, C. W. Woods, *J. Am. Chem. Soc.* 1960, 82, 4062-4066 and A. Carlsson, H. Corrodi, B. Waldeck *Helv. Chim. Acta* 1963, 46, 2271-2285 (Scheme 2, step a).

Scheme 2

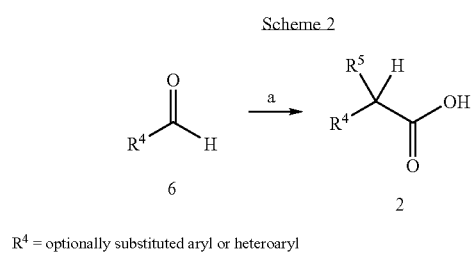

R⁴ = optionally substituted aryl or heteroaryl

An alternative way to the synthesis of -alkoxyaryl acetic acids 2 consists in lithiation of suitable compounds 7 with a strong base such as n-BuLi in an inert solvent like anhydrous THF or ether at low temperatures (e.g., −100° C.) under an atmosphere of nitrogen or argon. Slow addition of glyoxylic acid ethyl ester to a such generated lithium nucleophile generates —hydroxyaryl acetic acids of general structure 8 (Scheme 3, step a). Alkylation of hydroxy acids 8 can be conducted with suitable halides, mesylates, tosylates (or alcohols transformed into any other suitable leaving group X) in a solvent such as DMF, dichloromethane, dichloroethane or acetone at ambient or elevated temperatures using conventional heating or heating by microwave irradiation with the addition of a suitable tertiary amine base (e.g., triethylamine, N-ethyldiisopropylamine) or an inorganic base (e.g., $Cs_2CO_3$, $K_2CO_3$) or silver(I) oxide ($Ag_2O$) or by analogous alkylation reactions (Scheme 3, step b). Alternatively target structures of formula 9 might be accessible by Mitsunobu reaction (D. L. Hughes, The Mitsunobu Reaction, in *Organic Reactions*, Volume 42, 1992, John Wiley & Sons, New York; pp. 335-656) applying alcohols activated by a mixture of a phosphine like a trialkylphosphine such as tributylphosphine ((n-Bu)$_3$P), triphenylphosphine (Ph$_3$P) and the like and a diazo-compound like diethyl azodicarboxylate (DEAD), diisopropyl azodicarboxylate (DIAD) or di-tert-butyl azodicarboxylate and the like in a solvent commonly used for such transformations like THF, toluene, dichloromethane and the like. There is no particular restriction on the nature of the solvent to be employed, provided that it has no adverse effect on the reaction or the reagents involved and that it can dissolve the reagents, at least to some extent. The reaction can take place over a wide range of temperatures ranging from ambient temperature to the reflux temperature of the solvent employed. Ester hydrolysis of compounds 9 to give target structures 2 can be achieved applying standard reaction conditions used for such type of conversions known to a person skilled in the art such as stirring with alkaline hydroxides (e.g., LiOH, NaOH, KOH) in a solvent mixture consisting typically of THF and water at room temperature or elevated temperatures whereby conventional heating or heating by microwave irradiation might be applied.

Scheme 3

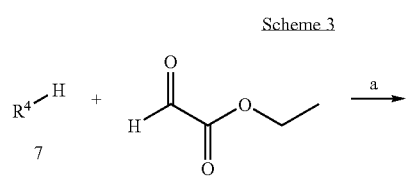

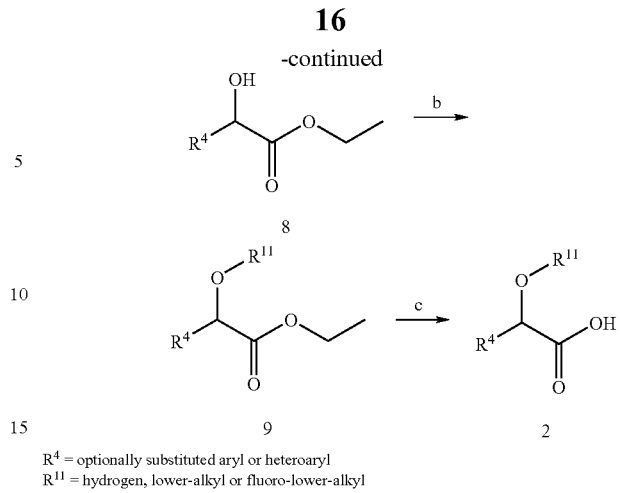

R⁴ = optionally substituted aryl or heteroaryl
R¹¹ = hydrogen, lower-alkyl or fluoro-lower-alkyl The isonitriles 3 can e.g., be obtained by dehydration of the corresponding formamide R¹—NH—CHO with a suitable reagent such as e.g., phosgene, POCl$_3$ or Me$_2$N=CH⁺Cl Cl⁻ or by reaction of the corresponding amine R¹—NH$_2$ with CHCl$_3$ and NaOH in a suitable solvent such as methanol. Aldehydes 4 are either commercially available or can be prepared by numerous methods known to the person skilled in the art. Appropriate synthesis methods include e.g., reduction of the corresponding carboxylic acid esters by a suitable reducing agent (e.g., diisobutylaluminium hydride at low temperature or with LiAlH$_4$ at elevated or ambient temperature) in a solvent followed by oxidation of the primary alcohol (e.g., with tetrapropylammonium perruthenate(VII), activated MnO$_2$ or Dess-Martin periodinane) to yield aldehydes 4. The 2-azidoarylamine 1 is usually prepared in three steps from the corresponding 2-aminoarylcarboxylic acid, which is converted into a 2-azidoarylcarboxylic acid by diazotation with NaNO$_2$ in a suitable solvent (e.g., methanol) and subsequent treatment with a suitable azide salt such as NaN$_3$ or TMSN$_3$. The resulting 2-azidoarylcarboxylic acid is then converted into 1 via Curtius rearrangement of the 2-azidoarylcarboxylic azide obtained from the 2-azidoarylcarboxylic acid by its activation with a suitable reagent (e.g., chloroethylformiate in the presence of a base such as triethylamine) and subsequent treatment with a suitable source of azide anions (e.g., NaN$_3$). The 2-azidoaryl amine 1 can alternatively be prepared via the 2-azidoarylcarboxamide obtained by activation of the 2-azidoarylcarboxylic acid with a suitable reagent (e.g., chloroethylformiate in the presence of a base such as triethylamine) and subsequent treatment with ammonia. This amide is converted into 1 in a so called Hofmann-rearrangement by treatment with a suitable reagent such as NaOBr.

If one of the starting materials or compounds of formula (I) contain one or more functional groups which are not stable or are reactive under the reaction conditions of one or more reaction steps, appropriate protecting groups (as described e.g., in "Protective Groups in Organic Chemistry" by T. W. Greene and P. G. M. Wutts, 2$^{nd}$ Ed., 1991, Wiley, New York) can be introduced before the critical step applying methods well known in the art. Such protecting groups can be removed at a later stage of the synthesis using standard methods described in the literature.

If compounds 1, 2, 3 or 4 contain stereogenic centers, compounds (I) can be obtained as mixtures of diastereomers or enantiomers, which can be separated by methods well known in the art, e.g., (chiral) HPLC or crystallization. Racemic compounds can e.g., be separated into their antipodes via diastereomeric salts by crystallization with optically pure acids or by separation of the antipodes by specific chromatographic methods using either a chiral adsorbens or a chiral eluent.

An alternative approach to the preparation of compounds of formula (I) is illustrated in Scheme 4.

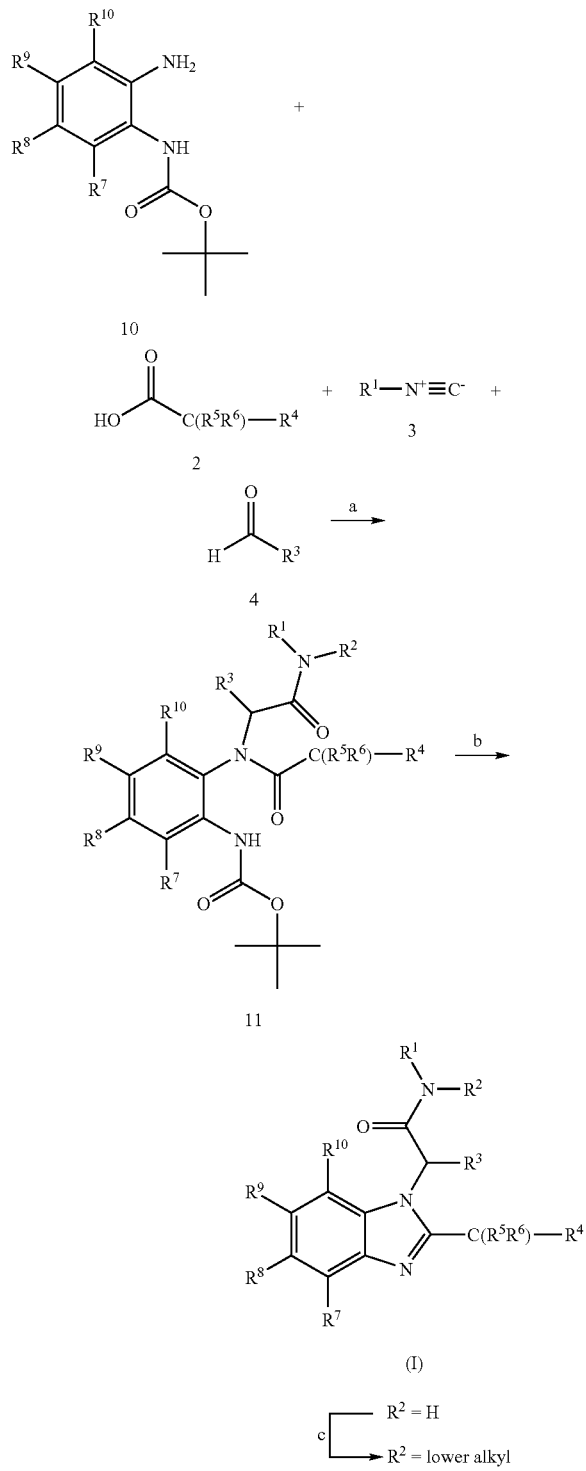

In this approach a mono boc-protected ortho arylene diamine 10, a carboxylic acid 2, an isonitrile 3, and an aldehyde 4 are condensed in an organic solvent such as e.g., methanol to provide the bis-amide 11 again in an Ugi-type condensation (Scheme 4, step a). Bis-amide 11 is then deprotected with TFA or HCl and spontaneously undergoes cyclization to the desired benzimidazole I (Scheme 4, step b), which can be optionally N-alkylated by deprotonation with a strong base (e.g., NaH or LiHMDA) and subsequent treatment with an alkylating agent $R^2$—X with X being a typical leaving group such as e.g., Cl, Br, I, $SO_2$alkyl, $SO_2$fluoroalkyl, $SO_2$aryl (Scheme 4, step c). Typical procedures applicable to this approach were described e.g., by P. Tempest, V. Ma, S. Thomas, Z. Hua, M. G. Kelly, C. Hulme *Tetrahedron Lett.* 2001, 42, 4959-4962 and P. Tempest, V. Ma, M. G. Kelly, W. Jones, C. Hulme *Tetrahedron Lett.* 2001, 42, 4963-4968 or by W. Zhang, P. Tempest *Tetrahedron Lett.* 2004, 45, 6757-6760. Mono boc-protected ortho arylene diamines 10 are commercially available or may be prepared from the corresponding unprotected diamine by treatment with di-tert-butyl dicarbonate in an organic solvent such as e.g., THF in the presence of a base such as e.g., diisopropylethylamine.

If desired or required functional groups present in I (such as —$CO_2$alkyl, amino groups, cyano groups and others) may be derivatized to other functional groups using typical standard procedures known to those skilled in the art (e.g., reduction of —$CO_2$alkyl to —$CH_2$OH with $LiAlH_4$, hydrolysis of —$CO_2$alkyl to $CO_2$H and subsequent optional conversion to an amide, acylation of amino groups).

If one of the starting materials or compounds of formula (I) contain one or more functional groups which are not stable or are reactive under the reaction conditions of one or more reaction steps, appropriate protecting groups (as described e.g., in "Protective Groups in Organic Chemistry" by T. W. Greene and P. G. M. Wutts, $2^{nd}$ Ed., 1991, Wiley, New York) can be introduced before the critical step applying methods well known in the art. Such protecting groups can be removed at a later stage of the synthesis using standard methods described in the literature.

If compounds 2, 3, 4 or 10 contain stereogenic centers, compounds (I) can be obtained as mixtures of diastereomers or enantiomers, which can be separated by methods well known in the art, e.g., (chiral) HPLC or crystallization. Racemic compounds can e.g., be separated into their antipodes via diastereomeric salts by crystallization with optically pure acids or by separation of the antipodes by specific chromatographic methods using either a chiral adsorbens or a chiral eluent.

$R^1$ as present in (I) after steps a and b or steps a, b and c in above shown schemes may be transformed into or replaced by other $R^1$ using one or a sequence of reaction steps. Two possible examples are given below:

a) $R^1$=$CH_2$Ph may for instance be removed using debenzylation conditions (e.g., hydrogenolysis in a solvent such as methanol in presence of a catalyst such as Pd(0) on charcoal powder) and a new $R^1$ can be introduced e.g., by deprotonation of the resulting $CONHR^2$ with a strong base (e.g., LiHMDA) and treatment with an alkylating agent $R^1$—X (X being a typical leaving group such as e.g., Cl, Br, I, $SO_2$alkyl, $SO_2$fluoroalkyl, $SO_2$aryl, and $R^1$ being $C_{1-10}$-alkyl, lower-alkoxy-lower-alkyl, lower-alkoxy-carbonyl-lower-alkyl, cycloalkyl, cycloalkyl-lower-alkyl, aryl-lower-alkyl, di-aryl-lower-alkyl, heteroaryl-lower-alkyl or heterocyclyl-lower-alkyl) or alternatively by a Pd(II)-promoted coupling with $R^1$—X ($R^1$ being aryl or heteroaryl and X being Cl, Br, I or $OSO_2CF_3$)

b) Amidolysis of the —CR³CONR¹R²-moiety of (I) to —CR³COOH may be carried out using suitable conditions such as heating in isopropanol in presence of NaOH or LiOH. A new amide bond can then be formed using an amine HNR¹R² and a typical peptide coupling reagent such as e.g., N,N'-carbonyldiimidazole (CDI), N,N'-dicyclohexylcarbodiimide (DCC), 1-(3-dimethyl-aminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyl-uronium tetrafluoroborate (TBTU) and the like. Preferred coupling agents are 1-(3-dimethylaminopropyl)-3-ethylcarbodiimide hydrochloride (EDCI) or N,N'-carbonyldiimidazole (CDI).

Functional groups present in (I) which are not stable or are reactive under the reaction conditions of one or more of the reaction steps, can be protected with appropriate protecting groups (as described e.g., in "Protective Groups in Organic Chemistry" by T. W. Greene and P. G. M. Wutts, 2$^{nd}$ Ed., 1991, Wiley, New York) before the critical step applying methods well known in the art. Such protecting groups can be removed at a later stage of the synthesis using standard methods described in the literature.

An alternative method for the amidolysis of Ugi reaction products is the treatment of benzimidazoles such as 12 with sodium nitrite in a mixture of acetic acid and acetic acid anhydride to give an intermediate diazotation reaction product which after rearrangement can be cleaved upon reaction with a mixture of alkaline hydroxides (e.g., LiOH, NaOH, KOH) and hydrogen peroxide to the corresponding free carboxylic acids 13 (Scheme 5, step a; see: E. H. White *J. Am. Chem. Soc.* 1955, 77, 6011-6014, D. A: Evans, P. H. Carter, C. J. Dinsmore, J. C. Barrow, J. L. Katz, D. W. Kung *Tetrahedron Lett.* 1997, 38, 4535-4538). The amide cleavage reaction is broad with respect to the nature of the amide that can be employed and is by no means limited to benzylamides only. The application of chiral acids in the Ugi reaction step leads to the formation of diastereoisomers, which might be separable by standard chromatography on normal silica either on the step of the amide 12 or the free acid 13. Alternatively, chiral acids 13 can be resolved by standard methods known to the person skilled in the art such as crystallization with chiral amines or by chiral chromatography.

Scheme 5

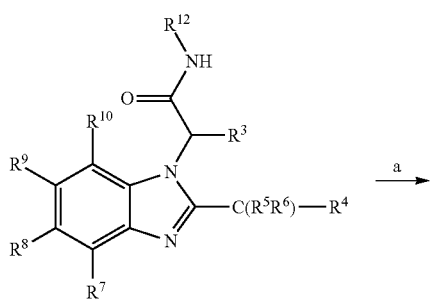

12

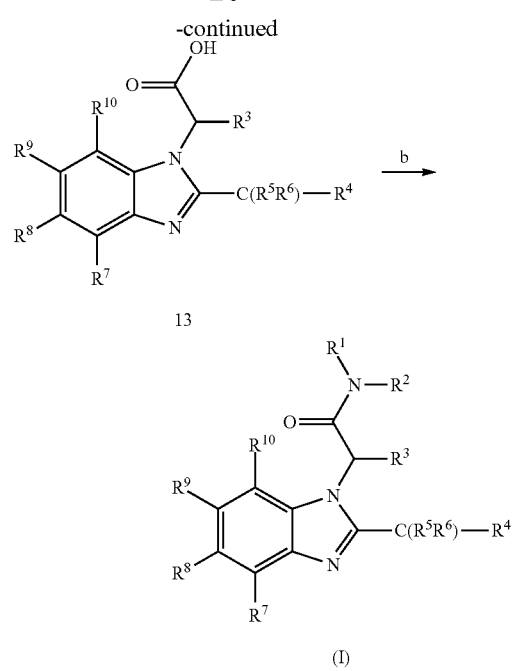

R¹² = protecting group, such as e.g. optionally substituted benzyl

The conversion of a compound of formula (I) into a pharmaceutically acceptable salt can be carried out by treatment of such a compound with an inorganic acid, for example a hydrohalic acid, such as, for example, hydrochloric acid or hydrobromic acid, or other inorganic acids such as sulfuric acid, nitric acid, phosphoric acid etc., or with an organic acid, such as, for example, acetic acid, citric acid, maleic acid, fumaric acid, tartaric acid, methanesulfonic acid or p-toluenesulfonic acid. The salts with an inorganic or organic acid can be obtained by standard methods known to the person skilled in the art, e.g., by dissolving the compound of formula (I) in a suitable solvent such as e.g., dioxane or THF and adding an appropriate amount of the corresponding acid. The products can conveniently be isolated by filtration or by chromatography. If an acidic group is present, the corresponding salts can be prepared from the compounds of formula (I) by treatment with physiologically compatible bases. One possible method to form such a salt is e.g., by addition of 1/n equivalents of a basic salt such as e.g., M(OH)$_n$, wherein M=metal or ammonium cation and n=number of hydroxide anions, to a solution of the compound in a suitable solvent (e.g., ethanol, ethanol-water mixture, tetrahydrofuran-water mixture) and to remove the solvent by evaporation or lyophilization.

The conversion of compounds of formula (I) into pharmaceutically acceptable esters can be carried out e.g., by treatment of hydroxy groups present in the molecules with a carboxylic acid such as acetic acid, with a condensating reagent such as benzotriazol-1-yloxytris(dimethylamino) phosphonium hexafluorophosphate (BOP), N,N-dicyclohexylcarbodiimide (DCC), N-(3-dimethylaminopropyl)-N'-ethylcarbodiimide hydrochloride (EDCI) or O-(1,2-dihydro-2-oxo-1-pyridyl)-N,N,N,N-tetra-methyluronium-tetrafluorborate (TPTU) to produce the carboxylic ester. Furthermore, carboxy groups present in the compounds of formula (I) can be reacted with suitable alcohols under analogous conditions as described above.

Insofar as their preparation is not described in the examples, the compounds of formula (I) as well as all intermediate products can be prepared according to analogous methods or according to the methods set forth above. Starting materials are commercially available, are known in the art, or can be prepared by methods analogous to those described herein.

As described above, the novel compounds of the present invention have been found to bind to and selectively activate FXR. They can therefore be used in the treatment and prophylaxis of diseases that are affected by FXR modulators, preferably FXR agonists. Such diseases include increased lipid and cholesterol levels, particularly high LDL-cholesterol, high triglycerides, low HDL-cholesterol, dyslipidemia, diseases of cholesterol absorption, atherosclerotic disease, peripheral occlusive disease, ischemic stroke, diabetes, particularly non-insulin dependent diabetes mellitus, metabolic syndrome, diabetic nephropathy, obesity, cholesterol gallstone disease, cholestasis/fibrosis of the liver, non-alcoholic steatohepatitis (NASH), non-alcoholic fatty liver disease (NAFLD), psoriasis, cancer, particularly gastrointestinal cancer, osteoporosis, Parkinson's disease, Alzheimer's disease.

The invention therefore also relates to pharmaceutical compositions comprising a compound as defined above and a pharmaceutically acceptable carrier and/or adjuvant.

The invention likewise embraces compounds as described above for use as therapeutically active substances, especially as therapeutically active substances for the treatment and/or prophylaxis of diseases that are affected by FXR modulators, preferably FXR agonists. Such diseases include increased lipid and cholesterol levels, particularly high LDL-cholesterol, high triglycerides, low HDL-cholesterol, dyslipidemia, diseases of cholesterol absorption, atherosclerotic disease, peripheral occlusive disease, ischemic stroke, diabetes, particularly non-insulin dependent diabetes mellitus, metabolic syndrome, diabetic nephropathy, obesity, cholesterol gallstone disease, cholestasis/fibrosis of the liver, non-alcoholic steatohepatitis (NASH), non-alcoholic fatty liver disease (NAFLD), psoriasis, cancer, particularly gastrointestinal cancer, osteoporosis, Parkinson's disease, Alzheimer's disease.

In another preferred embodiment, the invention relates to a method for the therapeutic and/or prophylactic treatment of diseases that are affected by FXR modulators, preferably FXR agonists. Such diseases include increased lipid and cholesterol levels, particularly high LDL-cholesterol, high triglycerides, low HDL-cholesterol, dyslipidemia, diseases of cholesterol absorption, atherosclerotic disease, peripheral occlusive disease, ischemic stroke, diabetes, particularly non-insulin dependent diabetes mellitus, metabolic syndrome, diabetic nephropathy, obesity, cholesterol gallstone disease, cholestasis/fibrosis of the liver, non-alcoholic steatohepatitis (NASH), non-alcoholic fatty liver disease (NAFLD), psoriasis, cancer, particularly gastrointestinal cancer, osteoporosis, Parkinson's disease, Alzheimer's disease, which method comprises administering a compound as defined above to a human being or animal.

The invention also embraces the use of compounds as defined above for the therapeutic and/or prophylactic treatment of diseases that are affected by FXR modulators, preferably FXR agonists. Such diseases include increased lipid and cholesterol levels, particularly high LDL-cholesterol, high triglycerides, low HDL-cholesterol, dyslipidemia, diseases of cholesterol absorption, atherosclerotic disease, peripheral occlusive disease, ischemic stroke, diabetes, particularly non-insulin dependent diabetes mellitus, metabolic syndrome, diabetic nephropathy, obesity, cholesterol gallstone disease, cholestasis/fibrosis of the liver, non-alcoholic steatohepatitis (NASH), non-alcoholic fatty liver disease (NAFLD), psoriasis, cancer, particularly gastrointestinal cancer, osteoporosis, Parkinson's disease, Alzheimer's disease.

The invention also relates to the use of compounds as described above for the preparation of medicaments for the therapeutic and/or prophylactic treatment of diseases which are modulated by FXR agonists, particularly for the therapeutic and/or prophylactic treatment of increased lipid and cholesterol levels, high LDL-cholesterol, high triglycerides, low HDL-cholesterol, dyslipidemia, atherosclerotic disease, diabetes, non-insulin dependent diabetes mellitus, metabolic syndrome, obesity, cholesterol gallstone disease, cholestasis/fibrosis of the liver, non-alcoholic steatohepatitis (NASH), non-alcoholic fatty liver disease (NAFLD), psoriasis, diseases of cholesterol absorption, cancer, gastrointestinal cancer, osteoporosis, peripheral occlusive disease, ischemic stroke, Parkinson's disease and/or Alzheimer's disease. Such medicaments comprise a compound as described above.

Prevention and/or treatment of high LDL cholesterol levels, high triglycerides, dyslipidemia, cholesterol gallstone disease, cancer, non-insulin dependent diabetes mellitus and metabolic syndrome is preferred, particularly high LDL cholesterol, high triglyceride levels and dyslipidemia.

The following tests were carried out in order to determine the activity of the compounds of formula (I). Background information on the binding assay can be found in: Nichols J S et al. "Development of a scintillation proximity assay for peroxisome proliferator-activated receptor gamma ligand binding domain", (1998) Anal. Biochem. 257: 112-119.

Bacterial and mammalian expression vectors were constructed to produce glutathione-s-transferase (GST) and Gal4 DNA binding domain (GAL) proteins fused to the ligand binding domain (LBD) of human FXR (aa 193-473). To accomplish this, the portions of the sequences encoding the FXR LBD were amplified by polymerase chain reaction (PCR) from a full-length clone by PCR and then subcloned into the plasmid vectors. The final clone was verified by DNA sequence analysis.

The induction, expression, and subsequent purification of GST-LBD fusion protein was performed in *E. coli* strain BL21(pLysS) cells by standard methods (Current Protocols in Molecular Biology, Wiley Press, ed. Ausubel et al.).

Radioligand Binding Assay

Binding of test substances to the FXR ligand binding domain was assessed in a radioligand displacement assay. The assay was performed in a buffer consisting of 50 mM Hepes, pH 7.4, 10 mM NaCl, 5 mM $MgCl_2$, 0.01% CHAPS. For each reaction well in a 96-well plate, 40 nM of GST-FXR LBD fusion protein was bound to 10 g glutathione yttrium silicate SPA beads (PharmaciaAmersham) in a final volume of 50 l by shaking A radioligand (e.g., 20 nM of 2,N-dicyclohexyl-2-[2-(2,4 dimethoxy-phenyl)-benzoimidazol-1-yl]-acetamide) and test compounds were added, and scintillation proximity counting was performed. All binding assays were performed in 96-well plates and the amount of bound ligand was measured on a Packard TopCount using OptiPlates (Packard). Dose response curves were performed within a range of test compound concentrations from $6\times10^{-9}$ M to $2.5\times10^{-5}$ M and $IC_{50}$ values were calculated.

Luciferase Transcriptional Reporter Gene Assays

Baby hamster kidney cells (BHK21 ATCC CCL10) were grown in DMEM medium containing 10% FBS at 37° C. in a 95% $O2$/5% $CO_2$ atmosphere. Cells were seeded in 6-well plates at a density of $10^5$ cells/well and then transfected with the pFA-FXR-LBD or expression plasmid plus a reporter plasmid. Transfection was accomplished with the Fugene 6 reagent (Roche Molecular Biochemicals) according to the suggested protocol. Six hours following transfection, the cells were harvested by trypsinization and seeded in 96-well plates at a density of $2\times10^5$ cells/well. After 24 hours to allow attachment of cells, the medium was removed and replaced with 100 l of phenol red-free medium containing the test substances or control ligands (final DMSO concentration: 0.4%). Following incubation of the cells for 24 hours with substances, 50 l of the supernatant was discarded and then 50 l of Luciferase Constant-Light Reagent (Roche Molecular Biochemicals) was added to lyse the cells and initiate the luciferase reaction. Luminescence, as a measure of luciferase activity, was detected in a Packard TopCount. Transcriptional activation in the presence of a test substance was expressed as fold-change in luminescence compared to that of cells incubated in the absence of the substance. $EC_{50}$ values were calculated using the XLfit program (ID Business Solutions Ltd. UK).

The compounds according to formula (I) have an activity in at least one of the above assays ($EC_{50}$ or $IC_{50}$), preferably of 0.1 nM to 10 M, more preferably 0.1 nM to 100 nM.

For example, the following compounds showed the following $EC_{50}$ and $IC_{50}$ values in the assays described above:

| Example | SPA binding $IC_{50}$ [M] |
|---|---|
| 1 | 0.013 |
| 2 | 0.006 |
| 3 | 0.030 |
| 4 | 0.032 |
| 5 | 0.032 |
| 6 | 0.073 |
| 7 | 0.004 |
| 8 | 9.505 |
| 9 | 0.029 |
| 10 | 0.705 |
| 11 | 0.010 |
| 12 | 0.357 |
| 13 | 0.153 |
| 14 | 0.219 |
| 15 | 0.037 |
| 16 | 0.596 |
| 17 | 0.906 |
| 18 | 0.860 |
| 19 | 0.129 |
| 20 | 0.902 |
| 21 | 0.009 |
| 22 | 0.009 |
| 23 | 0.010 |
| 24 | 0.057 |
| 25 | 0.002 |
| 26 | 0.094 |
| 27 | 0.016 |
| 28 | 0.034 |
| 29 | 0.029 |
| 30 | 0.0002 |
| 31 | 0.009 |
| 32 | 0.026 |
| 33 | 0.055 |
| 34 | 0.006 |
| 35 | 0.440 |
| 36 | 0.259 |
| 37 | 0.064 |
| 38 | 0.165 |
| 39 | 0.005 |
| 40 | 0.014 |
| 41 | 0.018 |
| 42 | 0.007 |
| 43 | 0.014 |
| 44 | 0.003 |
| 45 | 0.086 |
| 46 | 0.012 |
| 47 | 0.096 |
| 48 | 1.740 |
| 49 | 0.404 |
| 50 | 0.046 |
| 51 | 0.440 |
| 52 | 0.029 |
| 53 | 0.068 |
| 54 | 0.003 |
| 55 | 0.002 |
| 56 | 0.006 |
| 57 | 0.002 |
| 58 | 0.005 |
| 59 | 0.007 |
| 60 | 0.002 |
| 61 | 0.003 |
| 62 | 0.019 |
| 63 | 0.013 |
| 64 | 0.069 |
| 65 | 0.005 |
| 66 | 0.012 |
| 67 | 0.007 |
| 68 | 0.037 |
| 69 | 0.002 |
| 70 | 0.011 |
| 71 | 0.002 |
| 72 | 0.016 |
| 73 | 0.005 |
| 74 | 0.006 |
| 75 | 0.005 |
| 76 | 0.013 |
| 77 | 0.003 |
| 78 | 0.044 |
| 79 | 0.080 |
| 80 | 0.115 |
| 81 | 0.018 |
| 82 | 0.027 |
| 83 | 0.005 |
| 84 | 0.077 |
| 85 | 0.010 |
| 86 | 0.002 |
| 87 | 3.985 |
| 88 | 0.190 |
| 89 | 0.006 |
| 90 | 0.003 |
| 91 | 3.035 |
| 92 | 0.027 |
| 93 | 0.010 |
| 94 | 0.007 |
| 95 | 2.523 |
| 96 | 0.007 |
| 97 | 0.030 |
| 98 | 4.613 |
| 99 | 0.525 |
| 100 | 1.760 |
| 101 | 3.445 |

The compounds of formula I and/or their pharmaceutically acceptable salts can be used as medicaments, e.g., in the form of pharmaceutical preparations for enteral, parenteral or topical administration. They can be administered, for example, perorally, e.g., in the form of tablets, coated tablets, dragées, hard and soft gelatine capsules, solutions, emulsions or suspensions, rectally, e.g., in the form of suppositories, parenterally, e.g., in the form of injection solutions or suspensions or infusion solutions, or topically, e.g., in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g., in 1 to 3 dosage units.

The pharmaceutical preparations conveniently contain about 1-500 mg, preferably 1-100 mg, of a compound of formula I.

The following Examples serve to illustrate the present invention in more detail. They are, however, not intended to limit its scope in any manner.

EXAMPLES

Abbreviations

DMAP=4-dimethylaminopyridine, DMF=N,N-dimethylformamide, DMSO=dimethyl sulfoxide, NaHCO$_3$=sodium hydrogen carbonate, Na$_2$SO$_4$=sodium sulfate, h=hour, HATU=1-[bis(dimethylamino)methylene]-1H-1,2,3-triazolo[4,5-b]pyridinium-3-oxide hexafluorophosphate, HCl=hydrogen chloride, HPLC=high performance liquid chromatography, ISP=ion spray positive (mode), ISN=ion spray negative (mode), min=minutes, LiOH=lithium hydroxide, MS=mass spectrum, NH$_4$Cl=ammonium chloride, NMR=nuclear magnetic resonance, P=protecting group, R=any group, rt=room temperature, SiO$_2$=silica gel, THF=tetrahydrofuran, X=halogen.

General Remarks

Reactions were carried out under nitrogen or argon atmosphere, when appropriate. If not mentioned otherwise enantiomers or mixtures of diastereoisomers were used for in vitro profiling.

EXAMPLE 1

2-[2-(3-Chloro-benzyl)-5,6-difluoro-benzoimidazol-1-yl]-2,N-dicyclohexyl-acetamide Step 1

(2-Amino-4,5-difluoro-phenyl)-carbamic acid tert-butyl ester

To a solution of di-tert-butyl dicarbonate (14.8 g, 67.8 mmol, 2.0 equiv; [CAS RN 24424-99-5]) and 4-dimethylaminopyridine (0.21 g, 1.7 mmol, 0.05 equiv; DMAP; [CAS RN 1122-58-3]) in THF (100 mL) was added 4,5-difluoro-2-nitro-phenylamine (5.9 g, 33.9 mmol, 1.0 equiv; [CAS RN 78056-39-0]) and the mixture was stirred at rt for 72 h. The solvent was evaporated under reduced pressure and the crude reaction product extracted from a sat. solution of NaHCO$_3$ with ethyl acetate. The organic phases were dried over Na$_2$SO$_4$, the residue taken up in dichloromethane and cooled to 0° C. Trifluoroacetic acid (7.73 g, 67.8 mmol, 2.0 equiv) was added slowly and the reaction mixture stirred at 0° C. for 48 h. A solution of 2 N NaOH was added to adjust the pH of the solution to 7. The organic layer was separated and evaporated under reduced pressure. The residue was taken up in ethyl acetate and the product extracted from a sat. solution of NaHCO$_3$, the organic phase dried over Na$_2$SO$_4$ and the intermediate isolated via Kieselgel chromatography. The purified product (4.28 g, 15.6 mmol, 1.0 equiv) was dissolved in DMF (50 mL) and a sat. solution of NH$_4$Cl (13 mL) was added. Zinc powder (5.10 g, 78.0 mmol, 5.0 equiv) was added and the suspension stirred for 30 min at 80° C. and for an additional time period of 2 h at rt. The remaining solid was filtered off and the organic layer evaporated. The product was extracted from a sat. solution of NaHCO$_3$ with ethyl acetate, the organic layer dried over Na$_2$SO$_4$ and the crude reaction product purified via Kieselgel chromatography. $^1$H NMR (300 MHz, DMSO): 1.46 (s, 9H), 5.03 (br s, 2H), 6.65 (dd, J=8.2 Hz, J=12.9 Hz, 1H), 7.30 (dd, J=8.9 Hz, J=12.3 Hz, 1H), 8.38 (br s, 1H). MS (ISN): 243.4 [M−H]$^-$.

Step 2

To a solution of (2-amino-4,5-difluoro-phenyl)-carbamic acid tert-butyl ester (36.64 mg, 0.15 mmol, 1.0 equiv) in methanol (2.0 mL) was added cyclohexanecarbaldehyde (25.80 mg, 27.08 µL, 0.23 mmol, 1.5 equiv; [2043-61-0]) and the mixture stirred at rt. After 30 min, (3-chloro-phenyl)-acetic acid (34.12 mg, 0.20 mmol, 1.33 equiv; [CAS RN 1878-65-5]) and cyclohexyl isocyanide (16.38 mg, 18.41 µL, 0.15 mmol, 1.0 equiv; [931-53-3]) were added and stirring continued at rt for 2 h. A solution of 4 M HCl in dioxane (0.2 mL) was added and the reaction mixture stirred at rt overnight. Removal of the solvent mixture under reduced pressure and purification by preparative HPLC on reversed phase eluting with a gradient of acetonitrile/water provided 15.7 mg (21%) of the title compound. MS (ISP): 500.2 [M+H]$^+$.

EXAMPLE 2

2,N-Dicyclohexyl-2-[5,6-difluoro-2-(4-isopropyl-benzyl)-benzoimidazol-1-yl]-acetamide The title compound was prepared in analogy to Example 1, replacing (3-chloro-phenyl)-acetic acid with (4-isopropyl-phenyl)-acetic acid ([CAS RN 4476-28-2]). MS (ISP): 508.4 [M+H]$^+$.

EXAMPLE 3

2,N-Dicyclohexyl-2-[2-(4-ethoxy-benzyl)-5,6-difluoro-benzoimidazol-1-yl]-acetamide The title compound was prepared in analogy to Example 1, replacing (3-chloro-phenyl)-acetic acid with (4-ethoxy-phenyl)-acetic acid ([CAS RN 4919-33-9]). MS (ISP): 510.3 [M+H]$^+$.

EXAMPLE 4

2,N-Dicyclohexyl-2-[5,6-difluoro-2-(3-methoxy-benzyl)-benzoimidazol-1-yl]-acetamide The title compound was prepared in analogy to Example 1, replacing (3-chloro-phenyl)-acetic acid with (3-methoxy-phenyl)-acetic acid ([CAS RN 1798-09-0]). MS (ISP): 496.2 [M+H]$^+$.

EXAMPLE 5

2,N-Dicyclohexyl-2-[2-(3,4-dimethoxy-benzyl)-5,6-difluoro-benzoimidazol-1-yl]-acetamide The title compound was prepared in analogy to Example 1, replacing (3-chloro-phenyl)-acetic acid with (3,4-dimethoxy-phenyl)-acetic acid ([CAS RN 93-40-3]). MS (ISN): 526.0 [M+H]$^+$.

EXAMPLE 6

2,N-Dicyclohexyl-2-[5,6-difluoro-2-(2-hydroxy-benzyl)-benzoimidazol-1-yl]-acetamide The title compound was prepared in analogy to Example 1, replacing (3-chloro-phenyl)-acetic acid with (3-hydroxy-phenyl)-acetic acid ([CAS RN 621-37-4]). MS (ISP): 482.5 [M+H]$^+$.

EXAMPLE 7

2,N-Dicyclohexyl-2-[2-(2,4-difluoro-benzyl)-5,6-difluoro-benzoimidazol-1-yl]-acetamide The title compound was prepared in analogy to Example 1, replacing (3-chloro-phenyl)-acetic acid with (2,4-difluoro-phenyl)-acetic acid ([CAS RN 81228-09-3]). MS (ISP): 502.1 [M+H]$^+$.

EXAMPLE 8

2-{2-[(4-Chloro-phenyl)-hydroxy-methyl]-5,6-difluoro-benzoimidazol-1-yl}-2,N-dicyclohexyl-acetamide The title compound was prepared in analogy to Example 1, replacing (3-chloro-phenyl)-acetic acid with (4-chloro-phenyl)-hydroxy-acetic acid ([CAS RN 492-86-4]). MS (ISP): 516.2 [M+H]$^+$.

EXAMPLE 9

2-{2-[(R)-(4-Chloro-phenyl)-hydroxy-methyl]-5,6-difluoro-benzoimidazol-1-yl}-2,N-dicyclohexyl-acetamide The title compound was prepared in analogy to Example 1, replacing (3-chloro-phenyl)-acetic acid with (R)-(4-chloro-phenyl)-hydroxy-acetic acid ([CAS RN 32189-36-9]). MS (ISP): 516.3 [M+H]$^+$.

EXAMPLE 10

2,N-Dicyclohexyl-2-[5,6-difluoro-2-((S)-hydroxy-phenyl-methyl)-benzoimidazol-1-yl]-acetamide The title compound was prepared in analogy to Example 1, replacing (3-chloro-phenyl)-acetic acid with (S)-hydroxy-phenyl-acetic acid ([CAS RN 17199-29-0]). MS (ISP): 482.5 [M+H]$^+$.

EXAMPLE 11

(+)-2,N-Dicyclohexyl-2-[5,6-difluoro-2-((R)-hydroxy-phenyl-methyl)-benzoimidazol-1-yl]-acetamide The title compound was prepared in analogy to Example 1, replacing (3-chloro-phenyl)-acetic acid with (R)-hydroxy-phenyl-acetic acid ([CAS RN 611-71-2]). Separation of the stereoisomers was conducted by chiral preparative HPLC (Chiralcel OD) eluting with a gradient of isopropanol/heptane. MS (ISP): 482.5 [M+H]$^+$.

EXAMPLE 12

2,N-Dicyclohexyl-2-[5,6-difluoro-2-((S)-hydroxy-phenyl-methyl)-benzoimidazol-1-yl]-acetamide The title compound was prepared in analogy to Example 1, replacing (3-chloro-phenyl)-acetic acid with (S)-hydroxy-phenyl-acetic acid ([CAS RN 17199-29-0]). MS (ISP): 482.4 [M+H]$^+$.

EXAMPLE 13

2-{2-[(R)-(3-Chloro-phenyl)-hydroxy-methyl]-5,6-difluoro-benzoimidazol-1-yl}-2,N-dicyclohexyl-acetamide The title compound was prepared in analogy to Example 1, replacing (3-chloro-phenyl)-acetic acid with (R)-(3-chloro-phenyl)-hydroxy-acetic acid ([CAS RN 61008-98-8]). MS (ISP): 516.3 [M+H]$^+$.

EXAMPLE 14

2-{2-[(S)-(3-Chloro-phenyl)-hydroxy-methyl]-5,6-difluoro-benzoimidazol-1-yl}-2,N-dicyclohexyl-acetamide The title compound was prepared in analogy to Example 1, replacing (3-chloro-phenyl)-acetic acid with (S)-(3-chloro-phenyl)-hydroxy-acetic acid ([CAS RN 32222-43-8]). MS (ISP): 516.3 [M+H]$^+$.

EXAMPLE 15

2,N-Dicyclohexyl-2-{2-[(R)-(3,4-dichloro-phenyl)-hydroxy-methyl]-5,6-difluoro-benzoimidazol-1-yl}-acetamide The title compound was prepared in analogy to Example 1, replacing (3-chloro-phenyl)-acetic acid with (R)-(3,4-dichloro-phenyl)-hydroxy-acetic acid ([CAS RN 51359-76-3]). MS (ISP): 550.3 [M+H]$^+$.

EXAMPLE 16

2,N-Dicyclohexyl-2-{2-[(2,3-dichloro-phenyl)-hydroxy-methyl]-5,6-difluoro-benzoimidazol-1-yl}-acetamide The title compound was prepared in analogy to Example 1, replacing (3-chloro-phenyl)-acetic acid with (2,3-dichloro-phenyl)-hydroxy-acetic acid ([CAS RN 35599-91-8]). MS (ISP): 550.3 [M+H]$^+$.

EXAMPLE 17

2,N-Dicyclohexyl-2-[5,6-difluoro-2-(hydroxy-pyridin-2-yl-methyl)-benzoimidazol-1-yl]-acetamide The title compound was prepared in analogy to Example 1, replacing (3-chloro-phenyl)-acetic acid with hydroxy-pyridin-2-yl-acetic acid ([CAS RN 89791-91-3]). MS (ISP): 483.5 [M+H]$^+$.

EXAMPLE 18

2,N-Dicyclohexyl-2-[5,6-difluoro-2-(hydroxy-pyridin-3-yl-methyl)-benzoimidazol-1-yl]-acetamide The title compound was prepared in analogy to Example 1, replacing (3-chloro-phenyl)-acetic acid with hydroxy-pyridin-3-yl-acetic acid ([CAS RN 49769-60-0]). MS (ISP): 483.5 [M+H]$^+$.

EXAMPLE 19

2,N-Dicyclohexyl-2-{2-[1-(3,4-dichloro-phenyl)-1-hydroxy-ethyl]-5,6-difluoro-benzoimidazol-1-yl}-acetamide The title compound was prepared in analogy to Example 1, replacing (3-chloro-phenyl)-acetic acid with 2-(3,4-dichloro-phenyl)-2-hydroxy-propionic acid ([CAS RN 75122-96-2]). MS (ISP): 564.3 [M+H]$^+$.

EXAMPLE 20

2,N-Dicyclohexyl-2-[5,6-difluoro-2-(1-hydroxy-1-pyridin-2-yl-ethyl)-benzoimidazol-1-yl]-acetamide The title compound was prepared in analogy to Example 1, replacing (3-chloro-phenyl)-acetic acid with 2-hydroxy-2-pyridin-2-yl-propionic acid ([CAS RN 115919-16-9]). MS (ISP): 497.6 [M+H]$^+$.

EXAMPLE 21

2,N-Dicyclohexyl-2-[5,6-difluoro-2-(methoxy-phenyl-methyl)-benzoimidazol-1-yl]-acetamide The title compound was prepared in analogy to Example 1, replacing (3-chloro-phenyl)-acetic acid with methoxy-phenyl-acetic acid ([CAS RN 7021-09-2]). MS (ISP): 496.2 [M+H]$^+$.

EXAMPLE 22

2,N-Dicyclohexyl-2-[5,6-difluoro-2-((R)-methoxy-phenyl-methyl)-benzoimidazol-1-yl]-acetamide The title compound was prepared in analogy to Example 1, replacing (3-chloro-phenyl)-acetic acid with (R)-methoxy-phenyl-acetic acid ([CAS RN 3966-32-3]). MS (ISP): 496.6 [M+H]$^+$.

EXAMPLE 23

(−)-2,N-Dicyclohexyl-2-[5,6-difluoro-2-((R)-methoxy-phenyl-methyl)-benzoimidazol-1-yl]-acetamide The title compound was prepared in analogy to Example 1, replacing (3-chloro-phenyl)-acetic acid with (R)-methoxy-phenyl-acetic acid ([CAS RN 3966-32-3]). Separation of the stereoisomers was conducted by chiral preparative HPLC (Chiralpak AD) eluting with a gradient of isopropanol/heptane. MS (ISP): 496.5 [M+H]$^+$.

EXAMPLE 24

(+)-2-Cyclohexyl-N-cyclopentyl-2-[5,6-difluoro-2-((R)-methoxy-phenyl-methyl)-benzoimidazol-1-yl]-acetamide The title compound was prepared in analogy to Example 1, replacing (3-chloro-phenyl)-acetic acid with (R)-methoxy-phenyl-acetic acid ([CAS RN 3966-32-3]) and cyclohexyl isocyanide with cyclopentyl isocyanide ([CAS RN 68498-54-4]). Separation of the stereoisomers was conducted by chiral preparative HPLC (Chiralpak AD) eluting with a gradient of isopropanol/heptane. MS (ISP): 482.5 [M+H]$^+$.

EXAMPLE 25

(−)-(S)-2,N-Dicyclohexyl-2-[5,6-difluoro-2-((S)-methoxy-phenyl-methyl)-benzoimidazol-1-yl]-acetamide The title compound was prepared in analogy to Example 1, replacing (3-chloro-phenyl)-acetic acid with (S)-methoxy-phenyl-acetic acid ([CAS RN 26164-26-1]). Separation of the stereoisomers was conducted by chiral preparative HPLC (Chiralpak AD) eluting with a gradient of isopropanol/heptane. MS (ISP): 496.5 [M+H]$^+$.

EXAMPLE 26

(−)-(R)-2,N-Dicyclohexyl-2-[5,6-difluoro-2-((S)-methoxy-phenyl-methyl)-benzoimidazol-1-yl]-acetamide The title compound was prepared in analogy to Example 1, replacing (3-chloro-phenyl)-acetic acid with (S)-methoxyphenyl-acetic acid ([CAS RN 26164-26-1]). Separation of the stereoisomers was conducted by chiral preparative HPLC (Chiralpak AD) eluting with a gradient of isopropanol/heptane. MS (ISP): 496.6 [M+H]$^+$.

EXAMPLE 27

(−)-(S)-2-Cyclohexyl-N-cyclopentyl-2-[5,6-difluoro-2-((S)-methoxy-phenyl-methyl)-benzoimidazol-1-yl]-acetamide The title compound was prepared in analogy to Example 1, replacing (3-chloro-phenyl)-acetic acid with (S)-methoxy-phenyl-acetic acid ([CAS RN 26164-26-1]) and cyclohexyl isocyanide with cyclopentyl isocyanide ([CAS RN 68498-54-4]). Separation of the stereoisomers was conducted by chiral preparative HPLC (Chiralpak AD) eluting with a gradient of isopropanol/heptane. MS (ISP): 482.4 [M+H]$^+$.

EXAMPLE 28

(+)-(R)-2-Cyclohexyl-N-cyclopentyl-2-[5,6-difluoro-2-((S)-methoxy-phenyl-methyl)-benzoimidazol-1-yl]-acetamide The title compound was prepared in analogy to Example 1, replacing (3-chloro-phenyl)-acetic acid with (S)-methoxy-phenyl-acetic acid ([CAS RN 26164-26-1]) and cyclohexyl isocyanide with cyclopentyl isocyanide ([CAS RN 68498-54-4]). Separation of the stereoisomers was conducted by chiral preparative HPLC (Chiralpak AD) eluting with a gradient of isopropanol/heptane. MS (ISP): 482.4 [M+H]$^+$.

EXAMPLE 29

2-[2-(Benzo[1,3]dioxol-5-yl-methoxy-methyl)-5,6-difluoro-benzoimidazol-1-yl]-2,N-dicyclohexyl-acetamide The title compound was prepared in analogy to Example 1, replacing (3-chloro-phenyl)-acetic acid with benzo[1,3]dioxol-5-yl-methoxy-acetic acid ([CAS RN 112579-50-7]). MS (ISP): 540.5 [M+H]$^+$.

EXAMPLE 30

(−)-2-[2-(Benzo[1,3]dioxol-5-yl-methoxy-methyl)-5,6-difluoro-benzoimidazol-1-yl]-2,N-dicyclohexyl-acetamide The title compound was prepared in analogy to Example 1, replacing (3-chloro-phenyl)-acetic acid with benzo[1,3]dioxol-5-yl-methoxy-acetic acid ([CAS RN 112579-50-7]). Separation of the stereoisomers was conducted by chiral preparative HPLC (Chiralpak AD) eluting with a gradient of isopropanol/heptane. MS (ISP): 540.5 [M+H]$^+$.

EXAMPLE 31

(+)-2-[2-(Benzo[1,3]dioxol-5-yl-methoxy-methyl)-5,6-difluoro-benzoimidazol-1-yl]-2,N-dicyclohexyl-acetamide The title compound was prepared in analogy to Example 1, replacing (3-chloro-phenyl)-acetic acid with benzo[1,3]dioxol-5-yl-methoxy-acetic acid ([CAS RN 112579-50-7]). Separation of the stereoisomers was conducted by chiral preparative HPLC (Chiralpak AD) eluting with a gradient of isopropanol/heptane. MS (ISP): 540.5 [M+H]$^+$.

EXAMPLE 32

2,N-Dicyclohexyl-2-{5,6-difluoro-2-[(2-fluoro-5-methoxy-phenyl)-methoxy-methyl]-benzoimidazol-1-yl}-acetamide The title compound was prepared in analogy to Example 1, replacing (3-chloro-phenyl)-acetic acid with (2-fluoro-5-methoxy-phenyl)-methoxy-acetic acid (prepared from 2-fluoro-3-methoxybenzaldehyde [CAS RN 105728-90-3] following the general description described by A. Carlsson, H. Corrodi, B. Waldeck *Helv. Chim. Acta* 1963, 46, 2271-2285). MS (ISP): 544.4 [M+H]$^+$.

EXAMPLE 33

2,N-Dicyclohexyl-2-{5,6-difluoro-2-[(2-fluoro-4-methoxy-phenyl)-methoxy-methyl]-benzoimidazol-1-yl}-acetamide The title compound was prepared in analogy to Example 1, replacing (3-chloro-phenyl)-acetic acid with (2-fluoro-4-methoxy-phenyl)-methoxy-acetic acid ([CAS RN 701263-54-9]). MS (ISP): 544.4 [M+H]$^+$.

EXAMPLE 34

2,N-Dicyclohexyl-2-{2-[(3,5-difluoro-phenyl)-methoxy-methyl]-5,6-difluoro-benzoimidazol-1-yl}-acetamide The title compound was prepared in analogy to Example 1, replacing (3-chloro-phenyl)-acetic acid with (3,5-difluoro-phenyl)-methoxy-acetic acid ([CAS RN 253324-72-0]). MS (ISP): 532.4 [M+H]$^+$.

EXAMPLE 35

2,N-Dicyclohexyl-2-{2-[(4-ethoxy-2,6-difluoro-phenyl)-methoxy-methyl]-5,6-difluoro-benzoimidazol-1-yl}-acetamide Step 1
1-Ethoxy-3,5-difluoro-benzene [CAS RN 144891-25-8]

To a solution of 3,5-difluoro-phenol (10.0 g, 76.87 mmol, 1.0 equiv) and iodo-ethane (28.77 g, 14.91 mL, 184.49 mmol, 2.4 equiv) in acetone (150 mL) was added portionwise potassium carbonate (31.87 g, 230.6 mmol, 3.0 equiv) and the reaction mixture heated to reflux for 6 h. The reaction mixture was filtered, the filtrate poured into ice water and then extracted with ethyl acetate. The organic layer was washed with water, dried over $Na_2SO_4$ and concentrated by evaporation under reduced pressure yielding 7.60 g (63%) of the title compound.

$^1$H NMR (300 MHz, CDCl$_3$): 1.41 (t, J=7.5 Hz, 3H), 3.99 (q, J=7.5 Hz, 2H), 6.36-6.43 (m, 3H).

Step 2
(4-Ethoxy-2,6-difluoro-phenyl)-hydroxy-acetic acid ethyl ester

To a solution of 1-ethoxy-3,5-difluoro-benzene (7.50 g, 47.42 mmol, 1.0 equiv) and N-(2-dimethylamino-ethyl)-N, N',N'-trimethyl-ethane-1,2-diamine (8.63 g, 10.40 mL, 49.80 mmol, 1.05 equiv) in anhydrous THF (125 mL) was added n-BuLi (31.13 mL, 49.80 mmol, 1.05 equiv; 1.6 M solution in hexane) within 1 h at −100° C. A solution of glyoxylic acid ethyl ester (9.68 g, 94.85 mmol, 2.0 equiv) in toluene (19 mL) was slowly added over a time period of 45 min and stirring continued for 2 h at −100° C. The cooling bath was removed and at −30° C. a solution of 2 M HCl (105 mL) was added. The solution was concentrated by evaporation under reduced pressure and the reaction mixture extracted with ethyl acetate (3×100 mL). The combined organic phases were dried over MgSO$_4$ and concentrated by evaporation under reduced pressure. The crude material was purified by silica column chromatography using a MPLC system (CombiFlash Companion, Isco Inc.) eluting with a gradient of heptane/ethyl acetate to give 8.2 g (66%) of the title compound. $^1$H NMR (300 MHz, CDCl$_3$): 1.24 (t, J=7.5 Hz, 3H), 1.41 (t, J=7.5 Hz, 3H), 3.47 (d, J=6.0 Hz, 1H), 4.00 (q, J=7.5 Hz, 2H), 4.28 (q, J=7.5 Hz, 2H), 5.38 (d, J=6.0 Hz, 1H), 6.41-6.47 (m, 2H).

Step 3

(4-Ethoxy-2,6-difluoro-phenyl)-methoxy-acetic acid ethyl ester

To a solution of (4-ethoxy-2,6-difluoro-phenyl)-hydroxy-acetic acid ethyl ester (4.0 g, 15.37 mmol, 1.0 equiv) in toluene (50 mL) was added iodo-methane (21.82 g, 9.78 mL, 153.70 mmol, 10.0 equiv) and silver(I) oxide (7.12 g, 30.74 mmol, 2.0 equiv) and the reaction mixture heated to 60° C. for 18 h. The reaction mixture was filtered, the filtrate poured into ice water and then extracted with ethyl acetate. The organic layer was washed with water, dried over Na$_2$SO$_4$ and concentrated by evaporation under reduced pressure yielding 4.1 g (97%) of the title compound. $^1$H NMR (300 MHz, CDCl$_3$): 1.25 (t, J=7.5 Hz, 3H), 1.41 (t, J=7.5 Hz, 3H), 3.43 (s, 3H), 4.01 (q, J=7.5 Hz, 2H), 4.26 (q, J=7.5 Hz, 2H), 5.05 (s, 1H), 6.43-6.48 (m, 2H). MS (ISP): 292.3 [M+NH$_4$]$^+$.

Step 4

(4-Ethoxy-2,6-difluoro-phenyl)-methoxy-acetic acid

To (4-ethoxy-2,6-difluoro-phenyl)-methoxy-acetic acid ethyl ester (4.0 g, 14.58 mmol, 1.0 equiv), dissolved in THF (75 mL) and methanol (15 mL), was added a solution of 1 M LiOH (17.5 mL) and the reaction mixture stirred at rt for 4 h. A solution of 1 M HCl (25 mL) was added, the organic solvents removed by evaporation under reduced pressure and the residue extracted with ethyl acetate. The organic layer was washed with water, dried over Na$_2$SO$_4$ and concentrated by evaporation under reduced pressure yielding 3.5 g (98%) of the title compound.
$^1$H NMR (300 MHz, DMSO): 1.31 (t, J=7.5 Hz, 3H), 3.30 (s, 3H), 4.06 (q, J=7.5 Hz, 2H), 4.97 (s, 1H), 6.73-6.76 (m, 2H). MS (ISP): 245.3 [M−H]$^-$.

Step 5

The title compound was prepared in analogy to Example 1, replacing (3-chloro-phenyl)-acetic acid with (4-ethoxy-2,6-difluoro-phenyl)-methoxy-acetic acid. MS (ISP): 576.5 [M+H]$^+$.

EXAMPLE 36

2,N-Dicyclohexyl-2-{2-[(2,6-difluoro-phenyl)-methoxy-methyl]-5,6-difluoro-benzoimidazol-1-yl}-acetamide The title compound was prepared in analogy to Example 1, replacing (3-chloro-phenyl)-acetic acid with (2,6-difluoro-phenyl)-methoxy-acetic acid (prepared from 2,6-difluoro-benzaldehyde [CAS RN 437-81-0] following the general description described by A. Carlsson, H. Corrodi, B. Waldeck Helv. Chim. Acta 1963, 46, 2271-2285). MS (ISP): 532.3 [M+H]$^+$.

EXAMPLE 37

2,N-Dicyclohexyl-2-{2-[(2,3-difluoro-phenyl)-methoxy-methyl]-5,6-difluoro-benzoimidazol -1-yl}-acetamide The title compound was prepared in analogy to Example 1, replacing (3-chloro-phenyl)-acetic acid with (2,3-difluoro-phenyl)-methoxy-acetic acid (prepared from 2,3-difluoro-benzaldehyde [CAS RN 2646-91-5] following the general description described by A. Carlsson, H. Corrodi, B. Waldeck Helv. Chim. Acta 1963, 46, 2271-2285). MS (ISP): 532.4 [M+H]$^+$.

EXAMPLE 38

2,N-Dicyclohexyl-2-[5,6-difluoro-2-(2-hydroxy-1-phenyl-ethyl)-benzoimidazol-1-yl]-acetamide The title compound was prepared in analogy to Example 1, replacing (3-chloro-phenyl)-acetic acid with 3-hydroxy-2-phenyl-propionic acid ([CAS RN 552-63-6]). MS (ISP): 496.6 [M+H]$^+$.

EXAMPLE 39

2-[2-(3-Chloro-benzyl)-5-fluoro-benzoimidazol-1-yl]-2,N-dicyclohexyl-acetamide

To a solution of (2-amino-5-fluoro-phenyl)-carbamic acid tert-butyl ester (33.94 mg, 0.15 mmol, 1.0 equiv; prepared as described in M. J. Bamford, M. J. Alberti, N. Bailey, S. Davies, D. K. Dean, A. Gaiba, S. Garland, J. D. Harling, D. K. Jung, T. A. Panchal, C. A. Parr, J. G. Steadman, A. K. Takle, J. T. Townsend, D. M. Wilson, J. Witherington Bioorg. Med. Chem. Lett. 2005, 15, 3402-3406) in methanol (2.0 mL) was added cyclohexanecarbaldehyde (25.80 mg, 27.08 μL, 0.23 mmol, 1.5 equiv; [2043-61-0]) and the mixture stirred at rt. After 30 min, (3-chloro-phenyl)-acetic acid (34.12 mg, 0.20 mmol, 1.33 equiv; [CAS RN 1878-65-5]) and cyclohexyl isocyanide (16.38 mg, 18.41 μL, 0.15 mmol, 1.0 equiv; [931-53-3]) were added and stirring continued at rt for 2 h. A solution of 4 M HCl in dioxane (0.2 mL) was added and the reaction mixture stirred at rt overnight. Removal of the solvent mixture under reduced pressure and purification by preparative HPLC on reversed phase eluting with a gradient of acetonitrile/water provided 2.1 mg (3%) of the title compound. MS (ISP): 482.3 [M+H]$^+$.

EXAMPLE 40

2,N-Dicyclohexyl-2-[5-fluoro-2-(4-isopropyl-benzyl)-benzoimidazol-1-yl]-acetamide The title compound was prepared in analogy to Example 39, replacing (3-chloro-phenyl)-acetic acid with (4-isopropyl-phenyl)-acetic acid ([CAS RN 4476-28-2]). MS (ISP): 490.1 [M+H]$^+$.

EXAMPLE 41

2,N-Dicyclohexyl-2-[2-(4-ethoxy-benzyl)-5-fluoro-benzoimidazol-1-yl]-acetamide

The title compound was prepared in analogy to Example 39, replacing (3-chloro-phenyl)-acetic acid with (4-ethoxy-phenyl)-acetic acid ([CAS RN 4919-33-9]). MS (ISP): 492.3 [M+H]$^+$.

EXAMPLE 42

2,N-Dicyclohexyl-2-[5-fluoro-2-(3-methoxy-benzyl)-benzoimidazol-1-yl]-acetamide

The title compound was prepared in analogy to Example 39, replacing (3-chloro-phenyl)-acetic acid with (3-methoxy-phenyl)-acetic acid ([CAS RN 1798-09-0]). MS (ISP): 478.3 [M+H]+.

EXAMPLE 43

2,N-Dicyclohexyl-2-[2-(3,4-dimethoxy-benzyl)-5-fluoro-benzoimidazol-1-yl]-acetamide The title compound was prepared in analogy to Example 39, replacing (3-chloro-phenyl)-acetic acid with (3,4-dimethoxy-phenyl)-acetic acid ([CAS RN 93-40-3]). MS (ISP): 508.3 [M+H]+.

EXAMPLE 44

2,N-Dicyclohexyl-2-[2-(2,4-difluoro-benzyl)-5-fluoro-benzoimidazol-1-yl]-acetamide The title compound was prepared in analogy to Example 39, replacing (3-chloro-phenyl)-acetic acid with (2,4-difluoro-phenyl)-acetic acid ([CAS RN 81228-09-3]). MS (ISP): 484.3 [M+H]+.

EXAMPLE 45

2-{2-[(4-Chloro-phenyl)-hydroxy-methyl]-5-fluoro-benzoimidazol-1-yl}-2,N-dicyclohexyl -acetamide The title compound was prepared in analogy to Example 39, replacing (3-chloro-phenyl)-acetic acid with (4-chloro-phenyl)-hydroxy-acetic acid ([CAS RN 492-86-4]). MS (ISP): 498.3 [M+H]+.

EXAMPLE 46

2,N-Dicyclohexyl-2-[5-fluoro-2-(methoxy-phenyl-methyl)-benzoimidazol-1-yl]-acetamide The title compound was prepared in analogy to Example 39, replacing (3-chloro-phenyl)-acetic acid with methoxy-phenyl-acetic acid ([CAS RN 7021-09-2]). MS (ISP): 478.3 [M+H]+.

EXAMPLE 47

2-(2-Benzyl-6-chloro-5-fluoro-benzoimidazol-1-yl)-2,N-dicyclohexyl-acetamide

The title compound was prepared in analogy to Example 1, replacing (2-amino-4,5-difluoro-phenyl)-carbamic acid tert-butyl ester (Example 1, Step 1) with (2-amino-4-chloro-5-fluoro-phenyl)-carbamic acid tert-butyl ester ([CAS RN 579474-50-3]; prepared as described in WO 03/066 623 A1 (F. Hoffmann-La Roche AG)) and replacing (3-chloro-phenyl)-acetic acid with phenyl-acetic acid ([CAS RN 103-82-2]). MS (ISN): 480.3 [M−H]−.

EXAMPLE 48

2-[6-Chloro-5-fluoro-2-(hydroxy-phenyl-methyl)-benzoimidazol-1-yl]-2,N-dicyclohexyl -acetamide The title compound was prepared in analogy to Example 47, replacing phenyl-acetic acid with hydroxy-phenyl-acetic acid ([CAS RN 90-64-2]). MS (ISP): 497.6 [M+H]+.

EXAMPLE 49

2-(2-Benzyl-benzoimidazol-1-yl)-2,N-dicyclohexyl-acetamide

The title compound was prepared in analogy to Example 1, replacing (2-amino-4,5-difluoro-phenyl)-carbamic acid tert-butyl ester (Example 1, Step 1) with (2-amino-phenyl)-carbamic acid tert-butyl ester ([CAS RN 146651-75-4]; prepared as described by C. T. Seto, J. P. Mathias, G. M. Whitesides *J. Am. Chem. Soc.* 1993, 115, 1321-1329) and replacing (3-chloro-phenyl)-acetic acid with phenyl-acetic acid ([CAS RN 103-82-2]). MS (ISP): 430.5.

EXAMPLE 50

2-Cyclohexyl-2-[5-fluoro-2-((R)-methoxy-phenyl-methyl)-benzoimidazol-1-yl]-N-(4-hydroxy-cyclohexyl)-acetamide Step 1
N-Benzyl-2-cyclohexyl-2-[5-fluoro-2-((R)-methoxy-phenyl-methyl)-benzoimidazol-1-yl]-acetamide To a solution of (2-amino-5-fluoro-phenyl)-carbamic acid tert-butyl ester (4.0 g, 17.68 mmol, 1.0 equiv; prepared as described in M. J. Bamford, M. J. Alberti, N. Bailey, S. Davies, D. K. Dean, A. Gaiba, S. Garland, J. D. Harling, D. K. Jung, T. A. Panchal, C. A. Parr, J. G. Steadman, A. K. Takle, J. T. Townsend, D. M. Wilson, J. Witherington *Bioorg. Med. Chem. Lett.* 2005, 15, 3402-3406) in methanol (50 mL) was added cyclohexanecarbaldehyde (1.98 g, 2.13 mL, 17.68 mmol, 1.0 equiv; [2043-61-0]) and the mixture stirred at rt. After 30 min, (R)-methoxy-phenyl-acetic acid (2.94 g, 17.68 mmol, 1.0 equiv; [CAS RN 3966-32-3]) and isocyanomethyl-benzene (2.07 g, 2.15 mL, 17.68 mmol, 1.0 equiv; [931-53-3]) were added and stirring continued at rt for 2 h. A solution of 4 M HCl in dioxane (18 mL) was added and the reaction mixture stirred at rt overnight. The solution was concentrated by evaporation under reduced pressure, the pH adjusted to 9 by addition of a solution of 1 M NaHCO$_3$ and the aqueous layer extracted with dichloromethane. The combined organic phases were dried over MgSO$_4$ and concentrated by evaporation under reduced pressure. The crude material was purified by silica column chromatography using a MPLC system (CombiFlash Companion, Isco Inc.) eluting with a gradient of heptane (+1% triethylamine)/ethyl acetate to give 5.9 g (69%) of the title compound. $^1$H NMR (300 MHz, CDCl$_3$): 1.25 (t, J=7.5 Hz, 3H), 1.41 (t, J=7.5 Hz, 3H), 3.43 (s, 3H), 4.01 (q, J=7.5 Hz, 2H), 4.26 (q, J=7.5 Hz, 2H), 5.05 (s, 1H), 6.43-6.48 (m, 2H). MS (ISP): 486.4 [M+H]+.

Step 2
Cyclohexyl-[5-fluoro-2-((R)-methoxy-phenyl-methyl)-benzoimidazol-1-yl]-acetic acid To a solution of N-benzyl-2-cyclohexyl-2-[5-fluoro-2-((R)-methoxy-phenyl-methyl)-benzoimidazol -1-yl]-acetamide (5.91 g, 12.17 mmol, 1.0 equiv) in a mixture of acetic acid (40 mL) and acetic acid anhydride (80 mL) was added at 0° C. in several small portions sodium nitrite (18.47 g, 267.76 mmol, 22.0 equiv) within 1 h. The reaction mixture was stirred overnight allowing to warm up to rt. The solution was concentrated by evaporation under reduced pressure, the pH adjusted to 9 by addition of a solution of 1 M NaHCO$_3$ and the aqueous layer extracted with diethyl ether. The combined organic phases were dried over MgSO$_4$ and concentrated by evaporation under reduced pressure. The crude material was taken up in a mixture of THF:water (3:1, 40 mL) and a pre-prepared solution of LiOH (2.91 g, 121.71 mmol, 10.0 equiv) in hydrogen peroxide (2.76 g, 24.84 mL, 243.42 mmol, 20.0 equiv; 30% solution in water) was added and stirred at rt for 30 min. The solution was concentrated by evaporation under reduced pressure, the pH adjusted to 4 by addition of acetic acid and the aqueous layer extracted with diethyl ether. The combined organic phases were dried over MgSO$_4$ and concentrated by evaporation under reduced pressure. Purification by silica column chromatography using a MPLC system (CombiFlash Companion, Isco Inc.) eluting with a gradient of heptane (+1% acetic acid)/ethyl acetate yielded the title compound as two clean diastereoisomers in 1.52 g (32%, isomer A) and 1.50 g (31%, isomer B) together with a mixed fraction of 0.90 g (19%). Isomer A: MS (ISP): 397.3 [M+H]$^+$. Isomer B: MS (ISP): 397.1 [M+H]$^+$. Mixed fraction: MS (ISP): 397.1 [M+H]$^+$.

Step 3

To a solution of cyclohexyl-[5-fluoro-2-((R)-methoxy-phenyl-methyl)-benzoimidazol-1-yl]-acetic acid (100 mg, 0.25 mmol, 1.0 equiv) in DMF (1.5 mL) was added triethylamine (51.1 mg, 70.0 µL, 0.50 mmol, 2.0 equiv) and HATU (124.7 mg, 0.33 mmol, 1.3 equiv) and the mixture stirred at 40° C. After 15 min, trans-4-amino-cyclohexanol hydrochloride (50.03 mg, 0.33 mmol, 1.3 equiv; [CAS RN 50910-54-8]) was added and stirring continued at 50° C. for 2 h. Removal of the solvent mixture under reduced pressure and purification by preparative HPLC on reversed phase eluting with a gradient of acetonitrile/water provided 50 mg (40%) of the title compound. MS (ISP): 494.5 [M+H]$^+$.

EXAMPLE 51

2-Cyclohexyl-2-[5-fluoro-2-((R)-methoxy-phenyl-methyl)-benzoimidazol-1-yl]-N-(4-hydroxy-cyclohexyl)-acetamide The title compound was prepared in analogy to Example 50, replacing trans-4-amino-cyclohexanol hydrochloride with cis-4-amino-cyclohexanol ([CAS RN 40525-78-8]). MS (ISP): 494.5 [M+H]$^+$.

EXAMPLE 52

2-Cyclohexyl-N-cyclopentyl-2-[5-fluoro-2-((R)-methoxy-phenyl-methyl)-benzoimidazol-1-yl]-acetamide The title compound was prepared in analogy to Example 50, replacing trans-4-amino-cyclohexanol hydrochloride with cyclopentylamine ([CAS RN 1003-03-8]). MS (ISP): 464.4 [M+H]$^+$.

EXAMPLE 53

2-Cyclohexyl-2-[5,6-difluoro-2-((R)-methoxy-phenyl-methyl)-benzoimidazol-1-yl]-N-(4-hydroxy-cyclohexyl)-acetamide Step 1
N-Benzyl-2-cyclohexyl-2-[5,6-difluoro-2-((R)-methoxy-phenyl-methyl)-benzoimidazol-1-yl]-acetamide The title compound was prepared in analogy to Example 50, Step 1, replacing (2-amino-5-fluoro-phenyl)-carbamic acid tert-butyl ester with (2-amino-4,5-difluoro-phenyl)-carbamic acid tert-butyl ester (Example 1, Step 1) providing two clean diastereoisomers in 0.725 g (21%, isomer A, less polar isomer) and 0.695 g (20%, isomer B, more polar isomer) yield. Isomer A: MS (ISP): 504.4 [M+H]$^+$. Isomer B: MS (ISP): 504.4 [M+H]$^+$.

Step 2
Cyclohexyl-[5,6-difluoro-2-((R)-methoxy-phenyl-methyl)-benzoimidazol-1-yl]-acetic acid The title compound was prepared in analogy to Example 50, Step 2. Acid from Isomer A: MS (ISP): 415.3 [M+H]$^+$. Acid from Isomer B: MS (ISP): 415.3 [M+H]$^+$.

Step 3

The title compound was prepared in analogy to Example 50, Step 3 using the acid obtained from isomer B. MS (ISP): 512.5 [M+H]$^+$.

EXAMPLE 54

N-Cyclohexyl-2-[5,6-difluoro-2-(methoxy-phenyl-methyl)-benzoimidazol-1-yl]-2-(4-methoxy-phenyl)-acetamide Step 1
(2-Amino-4,5-difluoro-phenyl)-carbamic acid tert-butyl ester [CAS RN 1000698-88-3] (for alternative preparation see also Example 1, Step 1)

To a ice-bath cooled mixture of 1,2-diamino-4,5-difluorobenzene (10.00 g, 69 mmol, 1.0 equiv., [CAS RN 76179-40-3]) and di-tert-butyl-dicarbonate (12.87 g, 59 mmol, 0.85 equiv; [CAS RN 24424-99-5]) in absolute ethanol (150 mL) was added iodine (0.18 g, 0.007 mmol, 0.01 equiv; [CAS RN 7553-56-2]). The mixture was maintained overnight in the refrigerator. The solvent was evaporated under reduced pressure and the residue was purified by column chromatography on silica gel (500 g, 1:0→19:1 dichloromethane/ethyl acetate eluant) to afford, in order of elution, the bis-boc derivative as an orange solid (1.58 g, 6.6%), and the desired compound as a white solid (12.58 g, 74.2%).

Step 2

The title compound was prepared in analogy to Example 1, replacing cyclohexanecarbaldehyde with anisaldehyde ([CAS RN 123-11-5]) and (3-chloro-phenyl)-acetic acid with DL--methoxyphenylacetic acid ([CAS RN 7021-09-2]). MS (ISP): 520.3 [M+H]$^+$.

EXAMPLE 55

2-Benzo[1,3]dioxol-5-yl-N-cyclohexyl-2-[5,6-difluoro-2-(methoxy-phenyl-methyl)-benzoimidazol-1-yl]-acetamide The title compound was prepared in analogy to Example 1, replacing cyclohexanecarbaldehyde with piperonal ([CAS RN 120-57-0]) and (3-chloro-phenyl)-acetic acid with DL- -methoxyphenylacetic acid ([CAS RN 7021-09-2]). MS (ISP): 534.3 [M+H]⁺.

EXAMPLE 56

N-Cyclohexyl-2-[5,6-difluoro-2-(methoxy-phenyl-methyl)-benzoimidazol-1-yl]-3-(tetrahydro-thiopyran-4-yl)-propionamide The title compound was prepared in analogy to Example 1, replacing cyclohexanecarbaldehyde with tetrahydro-2H-thiopyran-4-acetaldehyde ([CAS RN 372159-78-9]) and (3-chloro-phenyl)-acetic acid with DL- -methoxyphenylacetic acid ([CAS RN 7021-09-2]). MS (ISP): 528.3 [M+H]⁺.

EXAMPLE 57

2-(3-Chloro-phenyl)-N-cyclohexyl-2-[5,6-difluoro-2-(methoxy-phenyl-methyl) -benzoimidazol-1-yl]-acetamide The title compound was prepared in analogy to Example 1, replacing cyclohexanecarbaldehyde with 3-chlorobenzaldehyde ([CAS RN 587-04-2]) and (3-chloro-phenyl)-acetic acid with DL- -methoxyphenylacetic acid ([CAS RN 7021-09-2]). MS (ISP): 524.3 [M+H]⁺.

EXAMPLE 58

N-Cyclohexyl-2-[2-(cyclohexyl-methoxy-methyl)-5,6-difluoro-benzoimidazol-1-yl]-2-(4-methoxy-phenyl)-acetamide The title compound was prepared in analogy to Example 1, replacing cyclohexanecarbaldehyde with anisaldehyde ([CAS RN 123-11-5]) and (3-chloro-phenyl)-acetic acid with DL-cyclohexyl-methoxy-acetic acid ([CAS RN 15540-18-8]). MS (ISP): 526.3 [M+H]⁺.

EXAMPLE 59

2-Benzo[1,3]dioxol-5-yl-N-cyclohexyl-2-[2-(cyclohexyl-methoxy-methyl)-5,6-difluoro -benzoimidazol-1-yl]-acetamide The title compound was prepared in analogy to Example 1, replacing cyclohexanecarbaldehyde with piperonal ([CAS RN 120-57-0]) and (3-chloro-phenyl)-acetic acid with DL-cyclohexyl-methoxy-acetic acid ([CAS RN 15540-18-8]). MS (ISP): 540.3 [M+H]⁺.

EXAMPLE 60

N-Cyclohexyl-2-[2-(cyclohexyl-methoxy-methyl)-5,6-difluoro-benzoimidazol-1-yl]-3-(tetrahydro-thiopyran-4-yl)-propionamide The title compound was prepared in analogy to Example 1, replacing cyclohexanecarbaldehyde with tetrahydro-2H-thiopyran-4-acetaldehyde ([CAS RN 372159-78-9]) and (3-chloro-phenyl)-acetic acid with DL-cyclohexyl-methoxy-acetic acid ([CAS RN 15540-18-8]). MS (ISP): 534.4 [M+H]⁺.

EXAMPLE 61

2-(3-Chloro-phenyl)-N-cyclohexyl-2-[2-(cyclohexyl-methoxy-methyl)-5,6-difluoro -benzoimidazol-1-yl]-acetamide The title compound was prepared in analogy to Example 1, replacing cyclohexanecarbaldehyde with 3-chlorobenzaldehyde ([CAS RN 587-04-2]) and (3-chloro-phenyl)-acetic acid with DL-cyclohexyl-methoxy-acetic acid ([CAS RN 15540-18-8]). MS (ISP): 530.3 [M+H]⁺.

EXAMPLE 62

N-Cyclopentyl-2-[5,6-difluoro-2-(methoxy-phenyl-methyl)-benzoimidazol-1-yl]-2-(4-methoxy-phenyl)-acetamide The title compound was prepared in analogy to Example 1, replacing cyclohexanecarbaldehyde with anisaldehyde ([CAS RN 123-11-5]), (3-chloro-phenyl)-acetic acid with DL- -methoxyphenylacetic acid ([CAS RN 7021-09-2]) and cyclohexyl isocyanide with cyclopentyl isocyanide ([CAS RN 68498-54-4]). MS (ISP): 506.3 [M+H]⁺.

EXAMPLE 63

2-Benzo[1,3]dioxol-5-yl-N-cyclopentyl-2-[5,6-difluoro-2-(methoxy-phenyl-methyl) -benzoimidazol-1-yl]-acetamide The title compound was prepared in analogy to Example 1, replacing cyclohexanecarbaldehyde with piperonal ([CAS RN 120-57-0]), (3-chloro-phenyl)-acetic acid with DL- -methoxyphenylacetic acid ([CAS RN 7021-09-2]) and cyclohexyl isocyanide with cyclopentyl isocyanide ([CAS RN 68498-54-4]). MS (ISP): 520.3 [M+H]⁺.

EXAMPLE 64

N-Cyclopentyl-2-[5,6-difluoro-2-(methoxy-phenyl-methyl)-benzoimidazol-1-yl]-3-(tetrahydro-thiopyran-4-yl)-propionamide The title compound was prepared in analogy to Example 1, replacing cyclohexanecarbaldehyde with tetrahydro-2H-thiopyran-4-acetaldehyde ([CAS RN 372159-78-9]), (3-chloro-phenyl)-acetic acid with DL- -methoxyphenylacetic acid ([CAS RN 7021-09-2]) and cyclohexyl isocyanide with cyclopentyl isocyanide ([CAS RN 68498-54-4]). MS (ISP): 514.3 [M+H]⁺.

EXAMPLE 65

2-(3-Chloro-phenyl)-N-cyclopentyl-2-[5,6-difluoro-2-(methoxy-phenyl-methyl) -benzoimidazol-1-yl]-acetamide The title compound was prepared in analogy to Example 1, replacing cyclohexanecarbaldehyde with 3-chlorobenzaldehyde ([CAS RN 587-04-2]), (3-chloro-phenyl)-acetic acid with DL- -methoxyphenylacetic acid ([CAS RN 7021-09-2])

EXAMPLE 66

2-[2-(Cyclohexyl-methoxy-methyl)-5,6-difluoro-benzoimidazol-1-yl]-N-cyclopentyl-2-(4-methoxy-phenyl)-acetamide The title compound was prepared in analogy to Example 1, replacing cyclohexanecarbaldehyde with anisaldehyde ([CAS RN 123-11-5]), (3-chloro-phenyl)-acetic acid with DL-cyclohexyl-methoxy-acetic acid ([CAS RN 15540-18-8]) and cyclohexyl isocyanide with cyclopentyl isocyanide ([CAS RN 68498-54-4]). MS (ISP): 512.3 [M+H]$^+$.

EXAMPLE 67

2-Benzo[1,3]dioxol-5-yl-2-[2-(cyclohexyl-methoxy-methyl)-5,6-difluoro-benzoimidazol-1-yl]-N-cyclo-pentyl-acetamide The title compound was prepared in analogy to Example 1, replacing cyclohexanecarbaldehyde with piperonal ([CAS RN 120-57-0]), (3-chloro-phenyl)-acetic acid with DL-cyclohexyl-methoxy-acetic acid ([CAS RN 15540-18-8]) and cyclohexyl isocyanide with cyclopentyl isocyanide ([CAS RN 68498-54-4]). MS (ISP): 526.3 [M+H]$^+$.

EXAMPLE 68

2-[2-(Cyclohexyl-methoxy-methyl)-5,6-difluoro-benzoimidazol-1-yl]-N-cyclopentyl-3-(tetrahydro-thiopyran-4-yl)-propionamide The title compound was prepared in analogy to Example 1, replacing cyclohexanecarbaldehyde with tetrahydro-2H-thiopyran-4-acetaldehyde ([CAS RN 372159-78-9]), (3-chloro-phenyl)-acetic acid with DL-cyclohexyl-methoxy-acetic acid ([CAS RN 15540-18-8]) and cyclohexyl isocyanide with cyclopentyl isocyanide ([CAS RN 68498-54-4]). MS (ISP): 520.3 [M+H]$^+$.

EXAMPLE 69

2-(3-Chloro-phenyl)-2-[2-(cyclohexyl-methoxy-methyl)-5,6-difluoro-benzoimidazol-1-yl]-N-cyclo-pentyl-acetamide The title compound was prepared in analogy to Example 1, replacing cyclohexanecarbaldehyde with 3-chlorobenzaldehyde ([CAS RN 587-04-2]), (3-chloro-phenyl)-acetic acid with DL-cyclohexyl-methoxy-acetic acid ([CAS RN 15540-18-8]) and cyclohexyl isocyanide with cyclopentyl isocyanide ([CAS RN 68498-54-4]). MS (ISP): 516.3 [M+H]$^+$.

EXAMPLE 70

2-[6-Chloro-5-fluoro-2-(methoxy-phenyl-methyl)-benzoimidazol-1-yl]-N-cyclohexyl-2-(4-methoxy-phenyl)-acetamide The title compound was prepared in analogy to Example 1, replacing (2-amino-4,5-difluoro-phenyl)-carbamic acid tert-butyl ester with (2-amino-4-chloro-5-fluoro-phenyl)-carbamic acid tert-butyl ester (([CAS RN 579474-50-3]), Example 47), cyclohexanecarbaldehyde with anisaldehyde ([CAS RN 123-11-5]) and (3-chloro-phenyl)-acetic acid with DL--methoxyphenylacetic acid ([CAS RN 7021-09-2]). MS (ISP): 536.3 [M+H]$^+$.

EXAMPLE 71

2-(6-Chloro-benzo[1,3]dioxol-5-yl)-2-[6-chloro-5-fluoro-2-(methoxy-phenyl-methyl)-benzoimidazol-1-yl]-N-cyclohexyl-acetamide The title compound was prepared in analogy to Example 1, replacing (2-amino-4,5-difluoro-phenyl)-carbamic acid tert-butyl ester with (2-amino-4-chloro-5-fluoro-phenyl)-carbamic acid tert-butyl ester (([CAS RN 579474-50-3]), Example 47), cyclohexanecarbaldehyde with piperonal ([CAS RN 120-57-0]) and (3-chloro-phenyl)-acetic acid with DL--methoxyphenylacetic acid ([CAS RN 7021-09-2]). MS (ISP): 584.2 [M+H]$^+$.

EXAMPLE 72

2-[6-Chloro-5-fluoro-2-(methoxy-phenyl-methyl)-benzoimidazol-1-yl]-N-cyclohexyl-3-(tetrahydro-thiopyran-4-yl)-propionamide The title compound was prepared in analogy to Example 1, replacing (2-amino-4,5-difluoro-phenyl)-carbamic acid tert-butyl ester with (2-amino-4-chloro-5-fluoro-phenyl)-carbamic acid tert-butyl ester (([CAS RN 579474-50-3]), Example 47), cyclohexanecarbaldehyde with tetrahydro-2H-thiopyran-4-acetaldehyde ([CAS RN 372159-78-9]) and (3-chloro-phenyl)-acetic acid with DL--methoxyphenylacetic acid ([CAS RN 7021-09-2]). MS (ISP): 544.3 [M+H]$^+$.

EXAMPLE 73

2-[6-Chloro-5-fluoro-2-(methoxy-phenyl-methyl)-benzoimidazol-1-yl]-2-(3-chloro-phenyl)-N-cyclo-hexyl-acetamide The title compound was prepared in analogy to Example 1, replacing (2-amino-4,5-difluoro-phenyl)-carbamic acid tert-butyl ester with (2-amino-4-chloro-5-fluoro-phenyl)-carbamic acid tert-butyl ester (([CAS RN 579474-50-3]), Example 47), cyclohexanecarbaldehyde with 3-chlorobenzaldehyde ([CAS RN 587-04-2]) and (3-chloro-phenyl)-acetic acid with DL--methoxyphenylacetic acid ([CAS RN 7021-09-2]). MS (ISP): 540.2 [M+H]$^+$.

EXAMPLE 74

2-[6-Chloro-2-(cyclohexyl-methoxy-methyl)-5-fluoro-benzoimidazol-1-yl]-N-cyclohexyl-2-(4-methoxy-phenyl)-acetamide The title compound was prepared in analogy to Example 1, replacing (2-amino-4,5-difluoro-phenyl)-carbamic acid tert-butyl ester with (2-amino-4-chloro-5-fluoro-phenyl)-carbamic acid tert-butyl ester (([CAS RN 579474-50-3]), Example 47), cyclohexanecarbaldehyde with anisaldehyde ([CAS RN 123-11-5]) and (3-chloro-phenyl)-acetic acid with DL-cyclohexyl-methoxy-acetic acid ([CAS RN 15540-18-8]). MS (ISP): 542.3 [M+H]$^+$.

EXAMPLE 75

2-Benzo[1,3]dioxol-5-yl-2-[6-chloro-2-(cyclohexyl-methoxy-methyl)-5-fluoro -benzoimidazol-1-yl]-N-cyclohexyl-acetamide The title compound was prepared in analogy to Example 1, replacing (2-amino-4,5-difluoro-phenyl)-carbamic acid tert-butyl ester with (2-amino-4-chloro-5-fluoro-phenyl)-carbamic acid tert-butyl ester (([CAS RN 579474-50-3]), Example 47), cyclohexanecarbaldehyde with piperonal ([CAS RN 120-57-0]) and (3-chloro-phenyl)-acetic acid with DL-cyclohexyl-methoxy-acetic acid ([CAS RN 15540-18-8]). MS (ISP): 556.3 [M+H]$^+$.

EXAMPLE 76

2-(6-Chloro-benzo[1,3]dioxol-5-yl)-2-[6-chloro-2-(cyclohexyl-methoxy-methyl)-5-fluoro -benzoimidazol-1-yl]-N-cyclohexyl-acetamide The title compound was prepared in analogy to Example 1, replacing (2-amino-4,5-difluoro-phenyl)-carbamic acid tert-butyl ester with (2-amino-4-chloro-5-fluoro-phenyl)-carbamic acid tert-butyl ester (([CAS RN 579474-50-3]), Example 47), cyclohexanecarbaldehyde with tetrahydro-2H-thiopyran-4-acetaldehyde ([CAS RN 372159-78-9]) and (3-chloro-phenyl)-acetic acid with DL-cyclohexyl-methoxy-acetic acid ([CAS RN 15540-18-8]). MS (ISP): 590.3 [M+H]$^+$.

EXAMPLE 77

2-[6-Chloro-2-(cyclohexyl-methoxy-methyl)-5-fluoro-benzoimidazol-1-yl]-2-(3-chloro -phenyl)-N-cyclohexyl-acetamide The title compound was prepared in analogy to Example 1, replacing (2-amino-4,5-difluoro-phenyl)-carbamic acid tert-butyl ester with (2-amino-4-chloro-5-fluoro-phenyl)-carbamic acid tert-butyl ester (([CAS RN 579474-50-3]), Example 47), cyclohexanecarbaldehyde with 3-chlorobenzaldehyde ([CAS RN 587-04-2]) and (3-chloro-phenyl)-acetic acid with DL-cyclohexyl-methoxy-acetic acid ([CAS RN 15540-18-8]). MS (ISP): 546.3 [M+H]$^+$.

EXAMPLE 78

2-[6-Chloro-5-fluoro-2-(methoxy-phenyl-methyl)-benzoimidazol-1-yl]-N-cyclopentyl-2-(4-methoxy-phenyl)-acetamide The title compound was prepared in analogy to Example 1, replacing (2-amino-4,5-difluoro-phenyl)-carbamic acid tert-butyl ester with (2-amino-4-chloro-5-fluoro-phenyl)-carbamic acid tert-butyl ester (([CAS RN 579474-50-3]), Example 47), cyclohexanecarbaldehyde with anisaldehyde ([CAS RN 123-11-5]), (3-chloro-phenyl)-acetic acid with DL- -methoxyphenylacetic acid ([CAS RN 7021-09-2]) and cyclohexyl isocyanide with cyclopentyl isocyanide ([CAS RN 68498-54-4]). MS (ISP): 522.3 [M+H]$^+$.

EXAMPLE 79

2-(6-Chloro-benzo[1,3]dioxol-5-yl)-2-[6-chloro-5-fluoro-2-(methoxy-phenyl-methyl) -benzoimidazol-1-yl]-N-cyclopentyl-acetamide The title compound was prepared in analogy to Example 1, replacing (2-amino-4,5-difluoro-phenyl)-carbamic acid tert-butyl ester with (2-amino-4-chloro-5-fluoro-phenyl)-carbamic acid tert-butyl ester (([CAS RN 579474-50-3]), Example 47), cyclohexanecarbaldehyde with piperonal ([CAS RN 120-57-0]), (3-chloro-phenyl)-acetic acid with DL- -methoxyphenylacetic acid ([CAS RN 7021-09-2]) and cyclohexyl isocyanide with cyclopentyl isocyanide ([CAS RN 68498-54-4]). MS (ISP): 570.2 [M+H]$^+$.

EXAMPLE 80

2-[6-Chloro-5-fluoro-2-(methoxy-phenyl-methyl)-benzoimidazol-1-yl]-N-cyclopentyl-3-(tetrahydro-thiopyran-4-yl)-propionamide The title compound was prepared in analogy to Example 1, replacing (2-amino-4,5-difluoro-phenyl)-carbamic acid tert-butyl ester with (2-amino-4-chloro-5-fluoro-phenyl)-carbamic acid tert-butyl ester (([CAS RN 579474-50-3]), Example 47), cyclohexanecarbaldehyde with tetrahydro-2H-thiopyran-4-acetaldehyde ([CAS RN 372159-78-9]), (3-chloro-phenyl)-acetic acid with DL- -methoxyphenylacetic acid ([CAS RN 7021-09-2]) and cyclohexyl isocyanide with cyclopentyl isocyanide ([CAS RN 68498-54-4]). MS (ISP): 530.3 [M+H]$^+$.

EXAMPLE 81

2-[6-Chloro-5-fluoro-2-(methoxy-phenyl-methyl)-benzoimidazol-1-yl]-2-(3-chloro-phenyl) -N-cyclopentyl-acetamide The title compound was prepared in analogy to Example 1, replacing (2-amino-4,5-difluoro-phenyl)-carbamic acid tert-butyl ester with (2-amino-4-chloro-5-fluoro-phenyl)-carbamic acid tert-butyl ester (([CAS RN 579474-50-3]), Example 47), cyclohexanecarbaldehyde with 3-chlorobenzaldehyde ([CAS RN 587-04-2]), (3-chloro-phenyl)-acetic acid with DL- -methoxyphenylacetic acid ([CAS RN 7021-09-2]) and cyclohexyl isocyanide with cyclopentyl isocyanide ([CAS RN 68498-54-4]). MS (ISP): 526.2 [M+H]$^+$.

EXAMPLE 82

2-[6-Chloro-2-(cyclohexyl-methoxy-methyl)-5-fluoro-benzoimidazol-1-yl]-N-cyclopentyl-2-(4-methoxy-phenyl)-acetamide The title compound was prepared in analogy to Example 1, replacing (2-amino-4,5-difluoro-phenyl)-carbamic acid tert-butyl ester with (2-amino-4-chloro-5-fluoro-phenyl)-carbamic acid tert-butyl ester (([CAS RN 579474-50-3]), Example 47), cyclohexanecarbaldehyde with anisaldehyde ([CAS RN 123-11-5]), (3-chloro-phenyl)-acetic acid with DL-cyclohexyl-methoxy-acetic acid ([CAS RN 15540-18-8]) and cyclohexyl isocyanide with cyclopentyl isocyanide ([CAS RN 68498-54-4]). MS (ISP): 528.3 [M+H]$^+$.

EXAMPLE 83

2-Benzo[1,3]dioxol-5-yl-2-[6-chloro-2-(cyclohexyl-methoxy-methyl)-5-fluoro -benzoimidazol-1-yl]-N-cyclopentyl-acetamide The title compound was prepared in analogy to Example 1, replacing (2-amino-4,5-difluoro-phenyl)-carbamic acid tert-butyl ester with (2-amino-4-chloro-5-fluoro-phenyl)-carbamic acid tert-butyl ester (([CAS RN 579474-50-3]), Example 47), cyclohexanecarbaldehyde with piperonal ([CAS RN 120-57-0]), (3-chloro-phenyl)-acetic acid with DL-cyclohexyl-methoxy-acetic acid ([CAS RN 15540-18-8]) and cyclohexyl isocyanide with cyclopentyl isocyanide ([CAS RN 68498-54-4]). MS (ISP): 542.3 [M+H]+.

EXAMPLE 84

2-[6-Chloro-2-(cyclohexyl-methoxy-methyl)-5-fluoro-benzoimidazol-1-yl]-N-cyclopentyl-3-(tetrahydro-thiopyran-4-yl)-propionamide The title compound was prepared in analogy to Example 1, replacing (2-amino-4,5-difluoro-phenyl)-carbamic acid tert-butyl ester with (2-amino-4-chloro-5-fluoro-phenyl)-carbamic acid tert-butyl ester (([CAS RN 579474-50-3]), Example 47), cyclohexanecarbaldehyde with tetrahydro-2H-thiopyran-4-acetaldehyde ([CAS RN 372159-78-9]), (3-chloro-phenyl)-acetic acid with DL-cyclohexyl-methoxy-acetic acid ([CAS RN 15540-18-8]) and cyclohexyl isocyanide with cyclopentyl isocyanide ([CAS RN 68498-54-4]). MS (ISP): 536.3 [M+H]+.

EXAMPLE 85

2-[6-Chloro-2-(cyclohexyl-methoxy-methyl)-5-fluoro-benzoimidazol-1-yl]-2-(3-chloro-phenyl)-N-cyclopentyl-acetamide The title compound was prepared in analogy to Example 1, replacing (2-amino-4,5-difluoro-phenyl)-carbamic acid tert-butyl ester with (2-amino-4-chloro-5-fluoro-phenyl)-carbamic acid tert-butyl ester (([CAS RN 579474-50-3]), Example 47), cyclohexanecarbaldehyde with 3-chlorobenzaldehyde ([CAS RN 587-04-2]), (3-chloro-phenyl)-acetic acid with DL-cyclohexyl-methoxy-acetic acid ([CAS RN 15540-18-8]) and cyclohexyl isocyanide with cyclopentyl isocyanide ([CAS RN 68498-54-4]). MS (ISP): 532.3 [M+H]+.

EXAMPLE 86

2,N-Dicyclohexyl-2-[2-(cyclohexyl-methoxy-methyl)-5,6-difluoro-benzoimidazol-1-yl]-acetamide The title compound was prepared in analogy to Example 1, replacing (3-chloro-phenyl)-acetic acid with DL-cyclohexyl-methoxy-acetic acid ([CAS RN 15540-18-8]). MS (ISP): 502.4 [M+H]+.

EXAMPLE 87

N-Cyclohexyl-2-[5,6-difluoro-2-((R)-2,2,2-trifluoro-1-methoxy-1-phenyl-ethyl)-benzoimidazol-1-yl]-2-(4-methoxy-phenyl)-acetamide The title compound was prepared in analogy to Example 1, replacing cyclohexanecarbaldehyde with anisaldehyde ([CAS RN 123-11-5]) and (3-chloro-phenyl)-acetic acid with (R)-(+)- -methoxy- -(trifluoromethyl)phenylacetic acid ([CAS RN 20445-31-2]). MS (ISP): 588.3 [M+H]+.

EXAMPLE 88

N-Cyclohexyl-2-[5,6-difluoro-2-((S)-2,2,2-trifluoro-1-methoxy-1-phenyl-ethyl)-benzoimidazol-1-yl]-2-(4-methoxy-phenyl)-acetamide The title compound was prepared in analogy to Example 1, replacing cyclohexanecarbaldehyde with anisaldehyde ([CAS RN 123-11-5]) and (3-chloro-phenyl)-acetic acid with (S)-(−)- -methoxy- -(trifluoromethyl)phenylacetic acid ([CAS RN 17257-71-5]). MS (ISP): 588.3 [M+H]+.

EXAMPLE 89

2-[2-(Benzo[1,3]dioxol-5-yl-methoxy-methyl)-5,6-difluoro-benzoimidazol-1-yl]-N -cyclohexyl-2-(4-methoxy-phenyl)-acetamide The title compound was prepared in analogy to Example 1, replacing cyclohexanecarbaldehyde with anisaldehyde ([CAS RN 123-11-5]) and (3-chloro-phenyl)-acetic acid with benzo[1,3]dioxol-5-yl-methoxy-acetic acid ([CAS RN 112579-50-7]). MS (ISP): 564.3 [M+H]+.

EXAMPLE 90

2-Cyclohexyl-2-[2-(cyclohexyl-methoxy-methyl)-5,6-difluoro-benzoimidazol-1-yl]-N -cyclopentyl-acetamide The title compound was prepared in analogy to Example 1, replacing (3-chloro-phenyl)-acetic acid with DL-cyclohexyl-methoxy-acetic acid ([CAS RN 15540-18-8]) and cyclohexyl isocyanide with cyclopentyl isocyanide ([CAS RN 68498-54-4]). MS (ISP): 488.4 [M+H]+.

EXAMPLE 91

N-Cyclopentyl-2-[5,6-difluoro-2-((S)-2,2,2-trifluoro-1-methoxy-1-phenyl-ethyl) -benzoimidazol-1-yl]-2-(4-methoxy-phenyl)-acetamide The title compound was prepared in analogy to Example 1, replacing cyclohexanecarbaldehyde with anisaldehyde ([CAS RN 123-11-5]), (3-chloro-phenyl)-acetic acid with (S)-(−)- -methoxy- -(trifluoromethyl)phenylacetic acid ([CAS RN 17257-71-5]) and cyclohexyl isocyanide with cyclopentyl isocyanide ([CAS RN 68498-54-4]). MS (ISP): 574.3 [M+H]+.

EXAMPLE 92

2-[2-(Benzo[1,3]dioxol-5-yl-methoxy-methyl)-5,6-difluoro-benzoimidazol-1-yl]-N -cyclopentyl-2-(4-methoxy-phenyl)-acetamide The title compound was prepared in analogy to Example 1, replacing cyclohexanecarbaldehyde with anisaldehyde ([CAS RN 123-11-5]), (3-chloro-phenyl)-acetic acid with benzo[1,3]dioxol-5-yl-methoxy-acetic acid ([CAS RN 112579-50-7]) and cyclohexyl isocyanide with cyclopentyl isocyanide ([CAS RN 68498-54-4]). MS (ISP): 550.3 [M+H]+.

EXAMPLE 93

N-Cyclohexyl-2-[5,6-difluoro-2-((S)-methoxy-phenyl-methyl)-benzoimidazol-1-yl]-2-(tetrahydro-thiopyran-4-yl)-acetamide The title compound was prepared in analogy to Example 1, replacing cyclohexanecarbaldehyde with tetrahydro-2H-thiopyran-4-carboxaldehyde ([CAS RN 50675-19-9]) and (3-chloro-phenyl)-acetic acid with (S)-methoxy-phenyl-acetic acid ([CAS RN 26164-26-1]). MS (ISP): 514.3 [M+H]$^+$.

EXAMPLE 94

N-Cyclohexyl-2-[5,6-difluoro-2-((S)-methoxy-phenyl-methyl)-benzoimidazol-1-yl]-3-(tetrahydro-thiopyran-4-yl)-propionamide The title compound was prepared in analogy to Example 1, replacing cyclohexanecarbaldehyde with tetrahydro-2H-thiopyran-4-acetaldehyde ([CAS RN 372159-78-9]) and (3-chloro-phenyl)-acetic acid with (S)-methoxy-phenyl-acetic acid ([CAS RN 26164-26-1]). MS (ISP): 528.4 [M+H]$^+$.

EXAMPLE 95

2-{Cyclohexylcarbamoyl-[5,6-difluoro-2-((S)-methoxy-phenyl-methyl)-benzoimidazol-1-yl]-methyl}-cyclopropanecarboxylic acid ethyl ester The title compound was prepared in analogy to Example 1, replacing cyclohexanecarbaldehyde with ethyl 2-formyl-1-cyclopropanecarboxylate ([CAS RN 20417-61-2]) and (3-chloro-phenyl)-acetic acid with (S)-methoxy-phenyl-acetic acid ([CAS RN 26164-26-1]). MS (ISP): 526.4 [M+H]$^+$.

EXAMPLE 96

N-Cyclohexyl-2-[5,6-difluoro-2-((R)-methoxy-phenyl-methyl)-benzoimidazol-1-yl]-2-(tetrahydro-thiopyran-4-yl)-acetamide The title compound was prepared in analogy to Example 1, replacing cyclohexanecarbaldehyde with tetrahydro-2H-thiopyran-4-carboxaldehyde ([CAS RN 50675-19-9]) and (3-chloro-phenyl)-acetic acid with (R)-methoxy-phenyl-acetic acid ([CAS RN 3966-32-3]). MS (ISP): 514.3 [M+H]$^+$.

EXAMPLE 97

N-Cyclohexyl-2-[5,6-difluoro-2-((R)-methoxy-phenyl-methyl)-benzoimidazol-1-yl]-3-(tetrahydro-thiopyran-4-yl)-propionamide The title compound was prepared in analogy to Example 1, replacing cyclohexanecarbaldehyde with tetrahydro-2H-thiopyran-4-acetaldehyde ([CAS RN 372159-78-9]) and (3-chloro-phenyl)-acetic acid with (R)-methoxy-phenyl-acetic acid ([CAS RN 3966-32-3]). MS (ISP): 528.4 [M+H]$^+$.

EXAMPLE 98

2-{Cyclohexylcarbamoyl-[5,6-difluoro-2-((R)-methoxy-phenyl-methyl)-benzoimidazol-1-yl]-methyl}-cyclopropanecarboxylic acid ethyl ester The title compound was prepared in analogy to Example 1, replacing cyclohexanecarbaldehyde with ethyl 2-formyl-1-cyclopropanecarboxylate ([CAS RN 20417-61-2]) and (3-chloro-phenyl)-acetic acid with (R)-methoxy-phenyl-acetic acid ([CAS RN 3966-32-3]). MS (ISP): 526.4 [M+H]$^+$.

EXAMPLE 99

N-Cyclohexyl-2-[5,6-difluoro-2-((S)-methoxy-phenyl-methyl)-benzoimidazol-1-yl]-2-(1,1-dioxo-hexahydro-1$^6$-thiopyran-4-yl)-acetamide To a solution of N-cyclohexyl-2-[5,6-difluoro-2-((S)-methoxy-phenyl-methyl) -benzoimidazol-1-yl]-2-(tetrahydro-thiopyran-4-yl)-acetamide (16 mg, 0.03 mmol, 1 equiv; Example 93) in ethyl acetate (0.5 mL) was added a solution of 39% peracetic acid in acetic acid (0.12 mL, 20 equiv). The solution was stirred at rt overnight and the solvent removed under reduced pressure. Toluene (0.5 mL) was added and the solution re-evaporated. The residue was purified by preparative HPLC on reverse phase eluting with a gradient of acetonitrile/water to afford the title compound as a yellow gum 16 mg (94%). MS (ISP): 546.3 [M+H]$^+$.

EXAMPLE 100

N-Cyclohexyl-2-[5,6-difluoro-2-((R)-methoxy-phenyl-methyl)-benzoimidazol-1-yl]-2-(1,1-dioxo-hexahydro-1$^6$-thiopyran-4-yl)-acetamide The title compound was prepared in analogy to Example 99, replacing N-cyclohexyl-2-[5,6-difluoro-2-((S)-methoxy-phenyl-methyl)-benzoimidazol-1-yl]-2-(tetrahydro-thiopyran-4-yl)-acetamide with N-cyclohexyl-2-[5,6-difluoro-2-((R)-methoxy-phenyl-methyl) -benzoimidazol-1-yl]-2-(tetrahydro-thiopyran-4-yl)-acetamide (Example 96). MS (ISP): 546.3 [M+H]$^+$.

EXAMPLE 101

N-Cyclohexyl-2-[5,6-difluoro-2-((R)-methoxy-phenyl-methyl)-benzoimidazol-1-yl]-3-(1,1-dioxo-hexahydro-1$^6$-thiopyran-4-yl)-propionamide The title compound was prepared in analogy to Example 99, replacing N-cyclohexyl-2-[5,6-difluoro-2-((S)-methoxy-phenyl-methyl)-benzoimidazol-1-yl]-2-(tetrahydro-thiopyran-4-yl)-acetamide with N-cyclohexyl-2-[5,6-difluoro-2-((R)-methoxy-phenyl-methyl) -benzoimidazol-1-yl]-3-(tetrahydro-thiopyran-4-yl)-propionamide (Example 97). MS (ISP): 560.4 [M+H]$^+$.

EXAMPLE A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |

-continued

| Ingredients | Per tablet | |
|---|---|---|
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aqueous solution/suspension of the above mentioned film coat.

EXAMPLE B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

EXAMPLE C

Injection solutions can have the following composition:

| | |
|---|---|
| Compound of formula (I) | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by acetic acid. The volume is adjusted to 1.0 mL by addition of the residual amount of water. The solution is filtered, filled into vials using an appropriate overage and sterilized.

EXAMPLE D

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |

-continued

| | |
|---|---|
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

EXAMPLE E

Sachets containing the following ingredients can be manufactured in a conventional manner:

| | |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidon K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavouring additives and filled into sachets.

The invention claimed is:
1. A compound selected from the group consisting of:
2,N-Dicyclohexyl-2-[5,6-difluoro-2-(hydroxy-pyridin-2-yl-methyl)-benzoimidazol-1-yl]-acetamide,
2,N-Dicyclohexyl-2-[5,6-difluoro-2-(hydroxy-pyridin-3-yl-methyl)-benzoimidazol-1-yl]-acetamide,
2,N-Dicyclohexyl-2-[5,6-difluoro-2-(1-hydroxy-1-pyridin-2-yl-ethyl)-benzoimidazol-1-yl]-acetamide,
2-[2-(Benzo[1,3]dioxol-5-yl-methoxy-methyl)-5,6-difluoro-benzoimidazol-1-yl]-2,N-dicyclohexyl-acetamide,
(−)-2-[2-(Benzo[1,3]dioxol-5-yl-methoxy-methyl)-5,6-difluoro-benzoimidazol-1-yl]-2,N-dicyclohexyl-acetamide,
(+)-2-[2-(Benzo[1,3]dioxol-5-yl-methoxy-methyl)-5,6-difluoro-benzoimidazol-1-yl]-2,N-dicyclohexyl-acetamide,
N-Cyclohexyl-2-[5,6-difluoro-2-(methoxy-phenyl-methyl)-benzoimidazol-1-yl]-2-(4-methoxy-phenyl)-acetamide,
2-Benzo[1,3]dioxol-5-yl-N-cyclohexyl-2-[5,6-difluoro-2-(methoxy-phenyl-methyl)-benzoimidazol-1-yl]-acetamide,
N-Cyclohexyl-2-[5,6-difluoro-2-(methoxy-phenyl-methyl)-benzoimidazol-1-yl]-3-(tetrahydro-thiopyran-4-yl)-propionamide,
2-(3-Chloro-phenyl)-N-cyclohexyl-2-[5,6-difluoro-2-(methoxy-phenyl-methyl)-benzoimidazol-1-yl]-acetamide,
N-Cyclohexyl-2-[2-(cyclohexyl-methoxy-methyl)-5,6-difluoro-benzoimidazol-1-yl]-2-(4-methoxy-phenyl)-acetamide,
2-Benzo[1,3]dioxol-5-yl-N-cyclohexyl-2-[2-(cyclohexyl-methoxy-methyl)-5,6-difluoro-benzoimidazol-1-yl]-acetamide,

N-Cyclohexyl-2-[2-(cyclohexyl-methoxy-methyl)-5,6-difluoro-benzoimidazol-1-yl]-3-(tetrahydro-thiopyran-4-yl)-propionamide, 2-(3-Chloro-phenyl)-N-cyclohexyl-2-[2-(cyclohexyl-methoxy-methyl)-5,6-difluoro-benzoimidazol-1-yl]-acetamide, N-Cyclopentyl-2-[5,6-difluoro-2-(methoxy-phenyl-methyl)-benzoimidazol-1-yl]-2-(4-methoxy-phenyl)-acetamide, 2-Benzo[1,3]dioxol-5-yl-N-cyclopentyl-2-[5,6-difluoro-2-(methoxy-phenyl-methyl)-benzoimidazol-1-yl]-acetamide, N-Cyclopentyl-2-[5,6-difluoro-2-(methoxy-phenyl-methyl)-benzoimidazol-1-yl]-3-(tetrahydro-thiopyran-4-yl)-propionamide, 2-(3-Chloro-phenyl)-N-cyclopentyl-2-[5,6-difluoro-2-(methoxy-phenyl-methyl)-benzoimidazol-1-yl]-acetamide, 2-[2-(Cyclohexyl-methoxy-methyl)-5,6-difluoro-benzoimidazol-1-yl]-N-cyclopentyl-2-(4-methoxy-phenyl)-acetamide, 2-Benzo[1,3]dioxol-5-yl-2-[2-(cyclohexyl-methoxy-methyl)-5,6-difluoro-benzoimidazol-1-yl]-N-cyclopentyl-acetamide, 2-[2-(Cyclohexyl-methoxy-methyl)-5,6-difluoro-benzoimidazol-1-yl]-N-cyclopentyl-3-(tetrahydro-thiopyran-4-yl)-propionamide, 2-(3-Chloro-phenyl)-2-[2-(cyclohexyl-methoxy-methyl)-5,6-difluoro-benzoimidazol-1-yl]-N-cyclopentyl-acetamide, 2-[6-Chloro-5-fluoro-2-(methoxy-phenyl-methyl)-benzoimidazol-1-yl]-N-cyclohexyl-2-(4-methoxy-phenyl)-acetamide, 2-(6-Chloro-benzo[1,3]dioxol-5-yl)-2-[6-chloro-5-fluoro-2-(methoxy-phenyl-methyl)-benzoimidazol-1-yl]-N-cyclohexyl-acetamide, 2-[6-Chloro-5-fluoro-2-(methoxy-phenyl-methyl)-benzoimidazol-1-yl]-N-cyclohexyl-3-(tetrahydro-thiopyran-4-yl)-propionamide, 2-[6-Chloro-5-fluoro-2-(methoxy-phenyl-methyl)-benzoimidazol-1-yl]-2-(3-chloro-phenyl)-N-cyclohexyl-acetamide, 2-[6-Chloro-2-(cyclohexyl-methoxy-methyl)-5-fluoro-benzoimidazol-1-yl]-N-cyclohexyl-2-(4-methoxy-phenyl)-acetamide, 2-Benzo[1,3]dioxol-5-yl-2-[6-chloro-2-(cyclohexyl-methoxy-methyl)-5-fluoro-benzoimidazol-1-yl]-N-cyclohexyl-acetamide, 2-(6-Chloro-benzo[1,3]dioxol-5-yl)-2-[6-chloro-2-(cyclohexyl-methoxy-methyl)-5-fluoro-benzoimidazol-1-yl]-N-cyclohexyl-acetamide, 2-[6-Chloro-2-(cyclohexyl-methoxy-methyl)-5-fluoro-benzoimidazol-1-yl]-2-(3-chloro-phenyl)-N-cyclohexyl-acetamide, 2-[6-Chloro-5-fluoro-2-(methoxy-phenyl-methyl)-benzoimidazol-1-yl]-N-cyclopentyl-2-(4-methoxy-phenyl)-acetamide, 2-(6-Chloro-benzo[1,3]dioxol-5-yl)-2-[6-chloro-5-fluoro-2-(methoxy-phenyl-methyl)-benzoimidazol-1-yl]-N-cyclopentyl-acetamide, 2-[6-Chloro-5-fluoro-2-(methoxy-phenyl-methyl)-benzoimidazol-1-yl]-N-cyclopentyl-3-(tetrahydro-thiopyran-4-yl)-propionamide, 2-[6-Chloro-5-fluoro-2-(methoxy-phenyl-methyl)-benzoimidazol-1-yl]-2-(3-chloro-phenyl)-N-cyclopentyl-acetamide, 2-[6-Chloro-2-(cyclohexyl-methoxy-methyl)-5-fluoro-benzoimidazol-1-yl]-N-cyclopentyl-2-(4-methoxy-phenyl)-acetamide, 2-Benzo[1,3]dioxol-5-yl-2-[6-chloro-2-(cyclohexyl-methoxy-methyl)-5-fluoro-benzoimidazol-1-yl]-N-cyclopentyl-acetamide, 2-[6-Chloro-2-(cyclohexyl-methoxy-methyl)-5-fluoro-benzoimidazol-1-yl]-N-cyclopentyl-3-(tetrahydro-thiopyran-4-yl)-propionamide, 2-[6-Chloro-2-(cyclohexyl-methoxy-methyl)-5-fluoro-benzoimidazol-1-yl]-2-(3-chloro-phenyl)-N-cyclopentyl-acetamide, 2,N-Dicyclohexyl-2-[2-(cyclohexyl-methoxy-methyl)-5,6-difluoro-benzoimidazol-1-yl]-acetamide, N-Cyclohexyl-2-[5,6-difluoro-2-((R)-2,2,2-trifluoro-1-methoxy-1-phenyl-ethyl)-benzoimidazol-1-yl]-2-(4-methoxy-phenyl)-acetamide, N-Cyclohexyl-2-[5,6-difluoro-2-((S)-2,2,2-trifluoro-1-methoxy-1-phenyl-ethyl)-benzoimidazol-1-yl]-2-(4-methoxy-phenyl)-acetamide, 2-[2-(Benzo[1,3]dioxol-5-yl-methoxy-methyl)-5,6-difluoro-benzoimidazol-1-yl]-N-cyclohexyl-2-(4-methoxy-phenyl)-acetamide, 2-Cyclohexyl-2-[2-(cyclohexyl-methoxy-methyl)-5,6-difluoro-benzoimidazol-1-yl]-N-cyclopentyl-acetamide, N-Cyclopentyl-2-[5,6-difluoro-2-((S)-2,2,2-trifluoro-1-methoxy-1-phenyl-ethyl)-benzoimidazol-1-yl]-2-(4-methoxy-phenyl)-acetamide, 2-[2-(Benzo[1,3]dioxol-5-yl-methoxy-methyl)-5,6-difluoro-benzoimidazol-1-yl]-N-cyclopentyl-2-(4-methoxy-phenyl)-acetamide, N-Cyclohexyl-2-[5,6-difluoro-2-((S)-methoxy-phenyl-methyl)-benzoimidazol-1-yl]-2-(tetrahydro-thiopyran-4-yl)-acetamide, N-Cyclohexyl-2-[5,6-difluoro-2-((S)-methoxy-phenyl-methyl)-benzoimidazol-1-yl]-3-(tetrahydro-thiopyran-4-yl)-propionamide, N-Cyclohexyl-2-[5,6-difluoro-2-((R)-methoxy-phenyl-methyl)-benzoimidazol-1-yl]-2-(tetrahydro-thiopyran-4-yl)-acetamide, N-Cyclohexyl-2-[5,6-difluoro-2-((R)-methoxy-phenyl-methyl)-benzoimidazol-1-yl]-3-(tetrahydro-thiopyran-4-yl)-propionamide, N-Cyclohexyl-2-[5,6-difluoro-2-((S)-methoxy-phenyl-methyl)-benzoimidazol-1-yl]-2-(1,1-dioxo-hexahydro-1-thiopyran-4-yl)-acetamide, N-Cyclohexyl-2-[5,6-difluoro-2-((R)-methoxy-phenyl-methyl)-benzoimidazol-1-yl]-2-(1,1-dioxo-hexahydro-1-thiopyran-4-yl)-acetamide, and N-Cyclohexyl-2-[5,6-difluoro-2-((R)-methoxy-phenyl-methyl)-benzoimidazol-1-yl]-3-(1,1-dioxo-hexahydro-1-thiopyran-4-yl)-propionamide, or a pharmaceutically acceptable salt or ester thereof.

2. A compound of claim 1 selected from the group consisting of:

2,N-Dicyclohexyl-2-[5,6-difluoro-2-(hydroxy-pyridin-2-yl-methyl)-benzoimidazol-1-yl]-acetamide, 2,N-Dicyclohexyl-2-[5,6-difluoro-2-(hydroxy-pyridin-3-yl-methyl)-benzoimidazol-1-yl]-acetamide, 2,N-Dicyclohexyl-2-[5,6-difluoro-2-(1-hydroxy-1-pyridin-2-yl-ethyl)-benzoimidazol-1-yl]-acetamide, 2-[2-(Benzo[1,3]dioxol-5-yl-methoxy-methyl)-5,6-difluoro-benzoimidazol-1-yl]-2,N-dicyclohexyl-acetamide, and (−)-2-[2-(Benzo[1,3]dioxol-5-yl-methoxy-methyl)-5,6-difluoro-benzoimidazol-1-yl]-2,N-dicyclohexyl-acetamide, or a pharmaceutically acceptable salt thereof.

3. A compound of claim 1 selected from the group consisting of:

(+)-2-[2-(Benzo[1,3]dioxol-5-yl-methoxy-methyl)-5,6-difluoro-benzoimidazol-1-yl]-2,N-dicyclohexyl-acetamide, N-Cyclohexyl-2-[5,6-difluoro-2-(methoxy-phenyl-methyl)-benzoimidazol-1-yl]-2-(4-methoxy-phenyl)-acetamide, 2-Benzo[1,3]dioxol-5-yl-N-cyclohexyl-2-[5,6-difluoro-2-(methoxy-phenyl-methyl)-benzoimidazol-1-yl]-acetamide, N-Cyclohexyl-2-[5,6-difluoro-2-(methoxy-phenyl-methyl)-benzoimidazol-1-yl]-3-(tetrahydro-thiopyran-4-yl)-propionamide, and 2-(3-Chloro-phenyl)-N-cyclohexyl-2-[5,6-difluoro-2-(methoxy-phenyl-methyl)-benzoimidazol-1-yl]-acetamide, or a pharmaceutically acceptable salt thereof.

4. A compound of claim 1 selected from the group consisting of:

N-Cyclohexyl-2-[2-(cyclohexyl-methoxy-methyl)-5,6-difluoro-benzoimidazol-1-yl]-2-(4-methoxy-phenyl)-acetamide, 2-Benzo[1,3]dioxol-5-yl-N-cyclohexyl-2-[2-(cyclohexyl-methoxy-methyl)-5,6-difluoro-benzoimidazol-1-yl]-acetamide, N-Cyclohexyl-2-[2-(cyclohexyl-methoxy-methyl)-5,6-difluoro-benzoimidazol-1-yl]-3-(tetrahydro-thiopyran-4-yl)-propionamide, 2-(3-Chloro-phenyl)-N-cyclohexyl-2-[2-(cyclohexyl-methoxy-methyl)-5,6-difluoro-benzoimidazol-1-yl]-acetamide, and N-Cyclopentyl-2-[5,6-difluoro-2-(methoxy-phenyl-methyl)-benzoimidazol-1-yl]-2-(4-methoxy-phenyl)-acetamide, or a pharmaceutically acceptable salt thereof.

5. A compound of claim 1 selected from the group consisting of:

2-Benzo[1,3]dioxol-5-yl-N-cyclopentyl-2-[5,6-difluoro-2-(methoxy-phenyl-methyl)-benzoimidazol-1-yl]-acetamide, N-Cyclopentyl-2-[5,6-difluoro-2-(methoxy-phenyl-methyl)-benzoimidazol-1-yl]-3-(tetrahydro-thiopyran-4-yl)-propionamide, 2-(3-Chloro-phenyl)-N-cyclopentyl-2-[5,6-difluoro-2-(methoxy-phenyl-methyl)-benzoimidazol-1-yl]-acetamide, 2-[2-(Cyclohexyl-methoxy-methyl)-5,6-difluoro-benzoimidazol-1-yl]-N-cyclopentyl-2-(4-methoxy-phenyl)-acetamide, and 2-Benzo[1,3]dioxol-5-yl-2-[2-(cyclohexyl-methoxy-methyl)-5,6-difluoro-benzoimidazol-1-yl]-N-cyclopentyl-acetamide, or a pharmaceutically acceptable salt thereof.

6. A compound of claim 1 selected from the group consisting of:

2-[2-(Cyclohexyl-methoxy-methyl)-5,6-difluoro-benzoimidazol-1-yl]-N-cyclopentyl-3-(tetrahydro-thiopyran-4-yl)-propionamide, 2-(3-Chloro-phenyl)-2-[2-(cyclohexyl-methoxy-methyl)-5,6-difluoro-benzoimidazol-1-yl]-N-cyclopentyl-acetamide, 2-[6-Chloro-5-fluoro-2-(methoxy-phenyl-methyl)-benzoimidazol-1-yl]-N-cyclohexyl-2-(4-methoxy-phenyl)-acetamide, 2-(6-Chloro-benzo[1,3]dioxol-5-yl)-2-[6-chloro-5-fluoro-2-(methoxy-phenyl-methyl)-benzoimidazol-1-yl]-N-cyclohexyl-acetamide, and 2-[6-Chloro-5-fluoro-2-(methoxy-phenyl-methyl)-benzoimidazol-1-yl]-N-cyclohexyl-3-(tetrahydro-thiopyran-4-yl)-propionamide, or a pharmaceutically acceptable salt thereof.

7. A compound of claim 1 selected from the group consisting of:

2-[6-Chloro-5-fluoro-2-(methoxy-phenyl-methyl)-benzoimidazol-1-yl]-2-(3-chloro-phenyl)-N-cyclohexyl-acetamide, 2-[6-Chloro-2-(cyclohexyl-methoxy-methyl)-5-fluoro-benzoimidazol-1-yl]-N-cyclohexyl-2-(4-methoxy-phenyl)-acetamide, 2-Benzo[1,3]dioxol-5-yl-2-[6-chloro-2-(cyclohexyl-methoxy-methyl)-5-fluoro-benzoimidazol-1-yl]-N-cyclohexyl-acetamide, 2-(6-Chloro-benzo[1,3]dioxol-5-yl)-2-[6-chloro-2-(cyclohexyl-methoxy-methyl)-5-fluoro-benzoimidazol-1-yl]-N-cyclohexyl-acetamide, and 2-[6-Chloro-2-(cyclohexyl-methoxy-methyl)-5-fluoro-benzoimidazol-1-yl]-2-(3-chloro-phenyl)-N-cyclohexyl-acetamide, or a pharmaceutically acceptable salt thereof.

8. A compound of claim 1 selected from the group consisting of:

2-[6-Chloro-5-fluoro-2-(methoxy-phenyl-methyl)-benzoimidazol-1-yl]-N-cyclopentyl-2-(4-methoxy-phenyl)-acetamide, 2-(6-Chloro-benzo[1,3]dioxol-5-yl)-2-[6-chloro-5-fluoro-2-(methoxy-phenyl-methyl)-benzoimidazol-1-yl]-N-cyclopentyl-acetamide, 2-[6-Chloro-5-fluoro-2-(methoxy-phenyl-methyl)-benzoimidazol-1-yl]-N-cyclopentyl-3-(tetrahydro-thiopyran-4-yl)-propionamide, 2-[6-Chloro-5-fluoro-2-(methoxy-phenyl-methyl)-benzoimidazol-1-yl]-2-(3-chloro-phenyl)-N-cyclopentyl-acetamide, and 2-[6-Chloro-2-(cyclohexyl-methoxy-methyl)-5-fluoro-benzoimidazol-1-yl]-N-cyclopentyl-2-(4-methoxy-phenyl)-acetamide, or a pharmaceutically acceptable salt thereof.

9. A compound of claim 1 selected from the group consisting of:

2-Benzo[1,3]dioxol-5-yl-2-[6-chloro-2-(cyclohexyl-methoxy-methyl)-5-fluoro-benzoimidazol-1-yl]-N-cyclopentyl-acetamide, 2-[6-Chloro-2-(cyclohexyl-methoxy-methyl)-5-fluoro-benzoimidazol-1-yl]-N-cyclopentyl-3-(tetrahydro-thiopyran-4-yl)-propionamide, 2-[6-Chloro-2-(cyclohexyl-methoxy-methyl)-5-fluoro-benzoimidazol-1-yl]-2-(3-chloro-phenyl)-N-cyclopentyl-acetamide, 2,N-Dicyclohexyl-2-[2-(cyclohexyl-methoxy-methyl)-5,6-difluoro-benzoimidazol-1-yl]-acetamide, and N-Cyclohexyl-2-[5,6-difluoro-2-((R)-2,2,2-trifluoro-1-methoxy-1-phenyl-ethyl)-benzoimidazol-1-yl]-2-(4-methoxy-phenyl)-acetamide, or a pharmaceutically acceptable salt thereof.

10. A compound of claim 1 selected from the group consisting of:
- N-Cyclohexyl-2-[5,6-difluoro-2-((S)-2,2,2-trifluoro-1-methoxy-1-phenyl-ethyl) -benzoimidazol-1-yl]-2-(4-methoxy-phenyl)-acetamide,
- 2-[2-(Benzo[1,3]dioxol-5-yl-methoxy-methyl)-5,6-difluoro-benzoimidazol-1-yl]-N -cyclohexyl-2-(4-methoxy-phenyl)-acetamide,
- 2-Cyclohexyl-2-[2-(cyclohexyl-methoxy-methyl)-5,6-difluoro-benzoimidazol-1-yl]-N -cyclopentyl-acetamide,
- N-Cyclopentyl-2-[5,6-difluoro-2-((S)-2,2,2-trifluoro-1-methoxy-1-phenyl-ethyl) -benzoimidazol-1-yl]-2-(4-methoxy-phenyl)-acetamide, and
- 2-[2-(Benzo[1,3]dioxol-5-yl-methoxy-methyl)-5,6-difluoro-benzoimidazol-1-yl]-N -cyclopentyl-2-(4-methoxy-phenyl)-acetamide, or a pharmaceutically acceptable salt thereof.

11. A compound of claim 1 selected from the group consisting of:
- N-Cyclohexyl-2-[5,6-difluoro-2-((S)-methoxy-phenyl-methyl)-benzoimidazol-1-yl]-2-(tetrahydro-thiopyran-4-yl)-acetamide,
- N-Cyclohexyl-2-[5,6-difluoro-2-((S)-methoxy-phenyl-methyl)-benzoimidazol-1-yl]-3-(tetrahydro-thiopyran-4-yl)-propionamide,
- N-Cyclohexyl-2-[5,6-difluoro-2-((R)-methoxy-phenyl-methyl)-benzoimidazol-1-yl]-2-(tetrahydro-thiopyran-4-yl)-acetamide, and
- N-Cyclohexyl-2-[5,6-difluoro-2-((R)-methoxy-phenyl-methyl)-benzoimidazol-1-yl]-3-(tetrahydro-thiopyran-4-yl)-propionamide, or a pharmaceutically acceptable salt thereof.

12. A compound of claim 1 selected from the group consisting of:
- N-Cyclohexyl-2-[5,6-difluoro-2-((S)-methoxy-phenyl-methyl)-benzoimidazol-1-yl]-2-(1,1-dioxo-hexahydro-1-thiopyran-4-yl)-acetamide,
- N-Cyclohexyl-2-[5,6-difluoro-2-((R)-methoxy-phenyl-methyl)-benzoimidazol-1-yl]-2-(1,1-dioxo-hexahydro-1-thiopyran-4-yl)-acetamide, and
- N-Cyclohexyl-2-[5,6-difluoro-2-((R)-methoxy-phenyl-methyl)-benzoimidazol-1-yl]-3-(1,1-dioxo-hexahydro-1-thiopyran-4-yl)-propionamide, or a pharmaceutically acceptable salt thereof.

13. A compound of claim 1 which is (−)-2-[2-(Benzo[1,3]dioxol-5-yl-methoxy-methyl)-5,6-difluoro-benzoimidazol-1-yl]-2,N-dicyclohexyl-acetamide.

14. A compound of claim 1 which is 2-(3-Chloro-phenyl)-N-cyclohexyl-2-[5,6-difluoro-2-(methoxy-phenyl-methyl)-benzoimidazol-1-yl]-acetamide.

15. A compound of claim 1 which is 2-(3-Chloro-phenyl)-N-cyclopentyl-2-[5,6-difluoro-2-(methoxy-phenyl-methyl)-benzoimidazol-1-yl]-acetamide.

16. A compound of claim 1 which is 2-(3-Chloro-phenyl)-2-[2-(cyclohexyl-methoxy-methyl)-5,6-difluoro-benzoimidazol-1-yl]-N-cyclopentyl-acetamide.

17. A compound of claim 1 which is 2-[6-Chloro-5-fluoro-2-(methoxy-phenyl-methyl) -benzoimidazol-1-yl]-2-(3-chloro-phenyl)-N-cyclohexyl-acetamide.

18. A compound of claim 1 which is 2,N-Dicyclohexyl-2-[2-(cyclohexyl-methoxy-methyl)-5,6-difluoro-benzoimidazol-1-yl]-acetamide.

19. A compound of claim 1 which is N-Cyclohexyl-2-[5,6-difluoro-2-((R)-methoxy-phenyl -methyl)-benzoimidazol-1-yl]-2-(tetrahydro-thiopyran-4-yl)-acetamide.

20. A pharmaceutical composition comprising a compound of claim 1 and a pharmaceutically acceptable carrier or adjuvant.

* * * * *